(12) United States Patent
Anderson et al.

(10) Patent No.: US 10,159,496 B2
(45) Date of Patent: Dec. 25, 2018

(54) METHOD, IMPLANT AND INSTRUMENTS FOR PERCUTANEOUS EXPANSION OF THE SPINAL CANAL

(71) Applicant: Innovative Surgical Designs, Inc., Bloomington, IN (US)

(72) Inventors: D. Greg Anderson, Moorestown, NJ (US); Wayne Beams, Bloomington, IN (US); Ed Morris, Bloomington, IN (US); Jonathan Rinehart, Bloomington, IN (US); Barry Turner, Columbus, IN (US)

(73) Assignee: Innovative Surgical Designs, Inc., Bloomington, IN (US)

( * ) Notice: Subject to any disclaimer, the term of this patent is extended or adjusted under 35 U.S.C. 154(b) by 496 days.

(21) Appl. No.: 14/641,034

(22) Filed: Mar. 6, 2015

(65) Prior Publication Data
US 2015/0272593 A1 Oct. 1, 2015

Related U.S. Application Data

(60) Provisional application No. 61/948,800, filed on Mar. 6, 2014, provisional application No. 61/948,924, filed on Mar. 6, 2014.

(51) Int. Cl.
*A61B 17/16* (2006.01)
*A61B 17/14* (2006.01)
(Continued)

(52) U.S. Cl.
CPC .......... *A61B 17/1671* (2013.01); *A61B 17/14* (2013.01); *A61B 50/30* (2016.02);
(Continued)

(58) Field of Classification Search
CPC . A61B 17/142; A61B 17/144; A61B 17/1671; A61B 2017/320028
See application file for complete search history.

(56) References Cited

U.S. PATENT DOCUMENTS 2,072,346 A  3/1934  Smith
5,591,170 A  1/1997  Spievack et al.
(Continued)

FOREIGN PATENT DOCUMENTS

WO  2014089198 A1  6/2014

OTHER PUBLICATIONS

International Search Report dated May 21, 2015; International Application No. PCT/US2015/019281; International Filing Date: Mar. 6, 2015; 7 pages.
(Continued)

*Primary Examiner* — Olivia C Chang
(74) *Attorney, Agent, or Firm* — Blank Rome LLP

(57) ABSTRACT

A bone saw and a method for using the bone saw. The bone saw includes a saw blade comprising a distal end, a proximal end, and a distal tip comprising a cutting edge. The flexible saw blade is rectangular in shape over at least a portion thereof. The bone saw further includes a saw handle base insert a saw shaft tip assembly comprising an opening through which the flexible saw blade is advanced. The saw shaft tip assembly may comprise a saw shaft tip comprising a channel comprising a distal end and a proximal end and a saw channel insert disposed within the channel of the saw shaft tip to form a lumen between the saw shift tip and the saw channel insert. The bone saw may further comprise a saw blade advancement mechanism coupled to the flexible saw blade for moving the flexible saw blade in discrete amounts.

21 Claims, 18 Drawing Sheets

(51) Int. Cl.
*A61B 50/30* (2016.01)
*A61B 50/33* (2016.01)
*A61B 17/32* (2006.01)

(52) U.S. Cl.
CPC .......... *A61B 50/33* (2016.02); *A61B 17/1604* (2013.01); *A61B 17/1659* (2013.01); *A61B 17/320016* (2013.01); *A61B 2050/3008* (2016.02)

(56) References Cited

U.S. PATENT DOCUMENTS

| | | |
|---|---|---|
| 5,827,305 A | 10/1998 | Gordon |
| 6,746,451 B2 | 6/2004 | Middleton et al. |
| 7,927,332 B2 | 4/2011 | Huebner et al. |
| 8,221,422 B2 | 7/2012 | Mangione |
| 8,394,102 B2 | 3/2013 | Garabedian et al. |
| 2006/0009796 A1 | 1/2006 | Carusillo et al. |
| 2007/0162131 A1* | 7/2007 | Friedman ................ A61F 2/442 623/17.11 |
| 2008/0033465 A1 | 2/2008 | Schmitz et al. |
| 2012/0245586 A1 | 9/2012 | Lehenkari et al. |
| 2013/0030456 A1* | 1/2013 | Assell ................ A61B 17/1617 606/170 |
| 2013/0197590 A1* | 8/2013 | Assell ............ A61B 17/320016 606/300 |
| 2013/0317509 A1 | 11/2013 | Anderson et al. |

OTHER PUBLICATIONS

Written Opinion dated May 21, 2015; International Application No. PCT/US2015/019281; International Filing Date: Mar. 6, 2015; 8 pages.

Extended European Search Report dated Oct. 2, 2017; European Application No. 15757809.7; Filing Date: Mar. 6, 2015; 7 pages.

\* cited by examiner

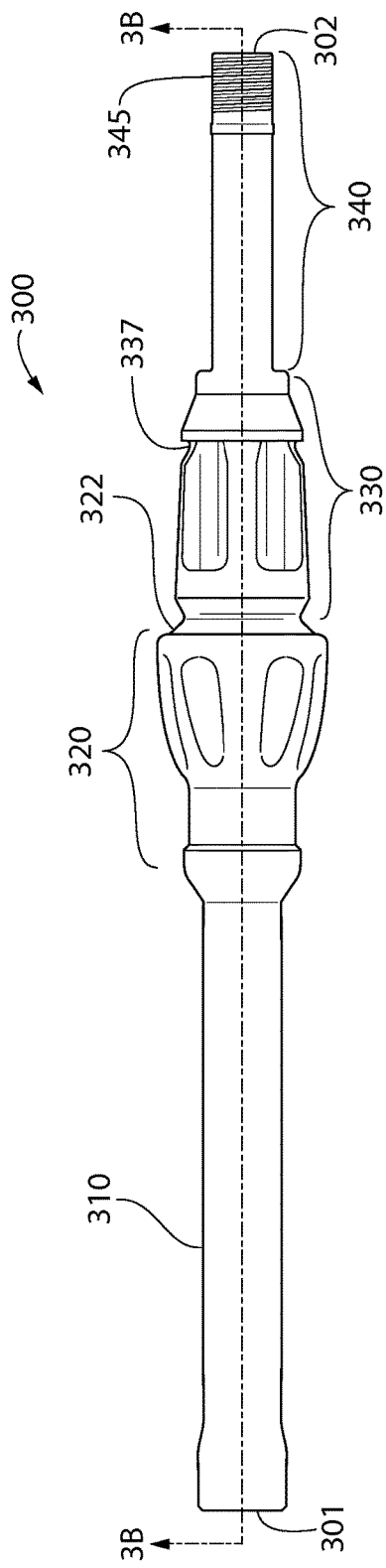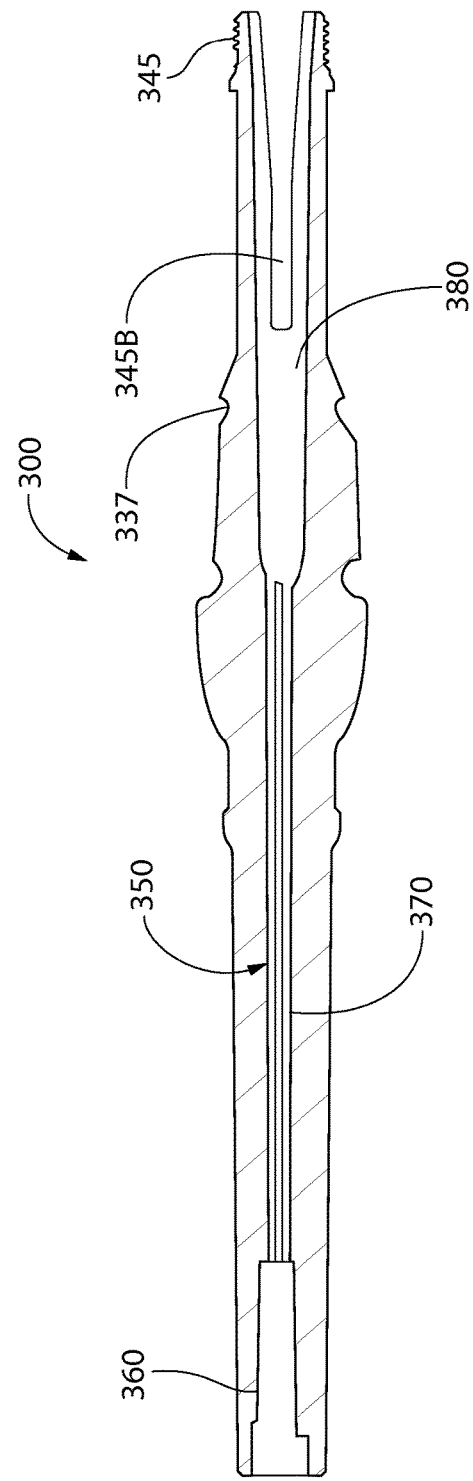
FIG. 3A
FIG. 3B

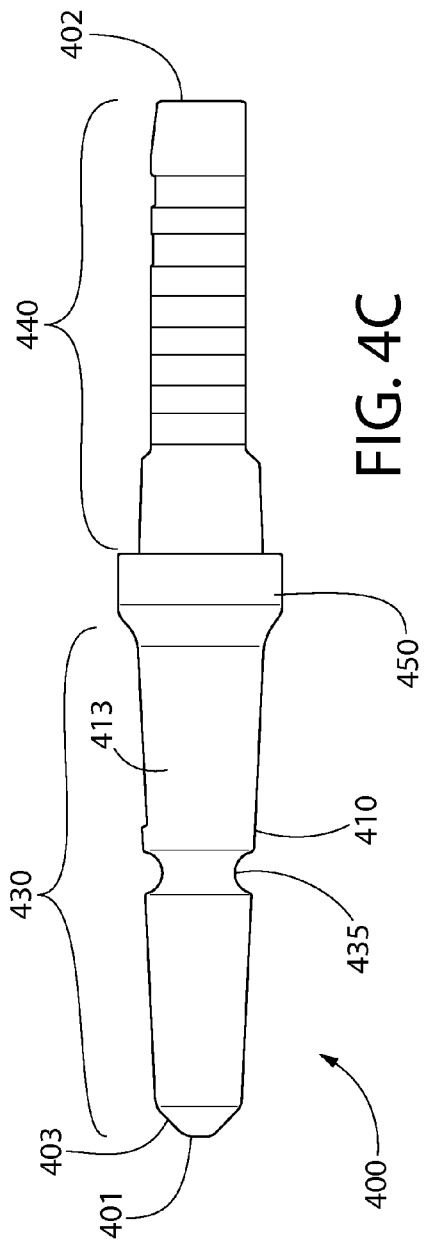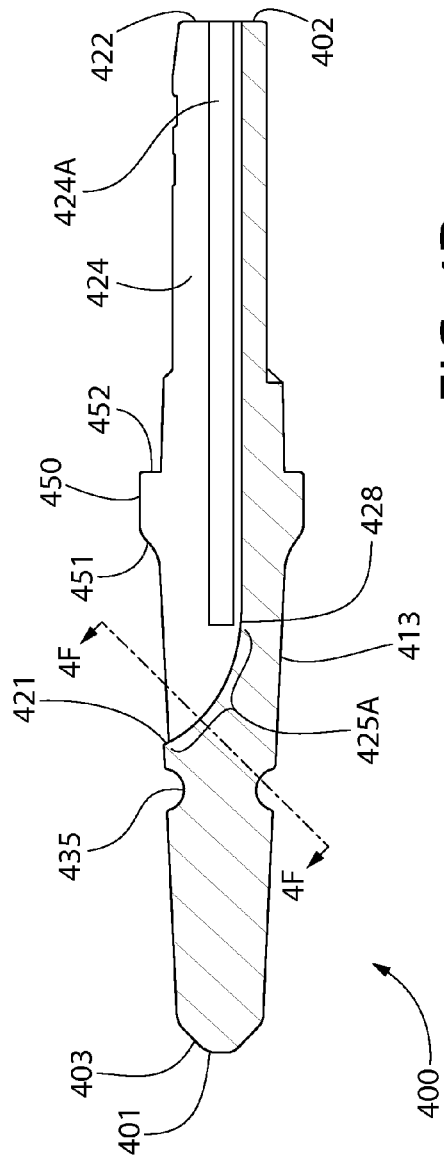

METHOD, IMPLANT AND INSTRUMENTS FOR PERCUTANEOUS EXPANSION OF THE SPINAL CANAL

CROSS REFERENCE TO RELATED APPLICATIONS

This application claims the benefit of U.S. Provisional Application No. 61/948,800, entitled "Instruments and Implants with Radiographic Markers Facilitating Percutaneous Method of Pedicle Lengthening" and filed Mar. 6, 2014, and the benefit of U.S. Provisional Application No. 61/948,924, entitled "Bone Saw for Percutaneous Method of Pedicle Lengthening" and filed Mar. 6, 2014, the contents of which applications are incorporated herein by reference.

FIELD OF THE INVENTION

The present invention relates generally to spinal surgery, and more particularly to a method and apparatus for expanding a spinal canal to relieve pressure on spinal nerves.

BACKGROUND OF THE INVENTION

Spinal stenosis, or narrowing of the spinal canal, inflicts millions of people with back and leg pain due to compression of spinal nerves. Severe spinal stenosis often leads to surgery in an effort to relieve compressed nerves and lessen back and leg pain. Spinal laminectomy is the traditional operation performed to treat spinal stenosis. In the spinal laminectomy, posterior aspects of the spinal column are removed to "un-roof" the spinal canal to relieve the pressure on the nerves. Specifically, a spinous process, lamina and portions of various facet joints are the posterior aspects of the spinal column surgically excised.

Although the spinal laminectomy is often successful in relieving pressure on the nerves of the spinal canal, several problems and disadvantages arise as a result of the laminectomy. First, the laminectomy removes important sites of back muscle attachment leading to back muscle dysfunction and pain. Second, the laminectomy exposes the nerve sac causing scar tissue to form around the nerves. Scar tissue may prevent normal motion of the nerves, leading to recurrent pain. Third, the laminectomy can destabilize the spine resulting in a forward slippage of one vertebra on another. Vertebral slippage can cause recurrent pain and deformity. Fourth, the laminectomy requires a large surgical exposure and significant blood loss, making the laminectomy dangerous for older patients. Finally, spinal stenosis can recur following the laminectomy, requiring risky revision surgery.

Laminectomy risks have led surgeons to seek an alternative for patients with severe spinal stenosis. Some surgeons choose to treat spinal stenosis with multiple laminotomies. Laminotomies involve removing bone and soft tissue from the posterior aspect of the spine making "windows" into the spinal canal over areas of nerve compression. Multiple laminotomies remove less tissue than the laminectomy, resulting in less scaring, vertebral instability and blood loss.

Multiple laminotomies, however, also suffer from problems and disadvantages. Laminotomies may not adequately relieve nerve compression and the pain may continue. Laminotomies are more difficult to correctly perform than the laminectomy. Laminotomies expose the nerves and may cause nerve scaring. Patients receiving multiple laminotomies also often have recurrent spinal stenosis requiring risky revision surgery.

For the foregoing reasons, there is a need for different and better methods for relieving the symptoms of spinal stenosis without the drawbacks of currently available techniques. A method is needed that expands the spinal canal, relieving pressure on the spinal nerves, while being simple, safe and permanent.

An initial invention was submitted by the present inventor entitled, "A Method and Implant for Expanding the Spinal Canal" (now U.S. Pat. No. 6,358,254). In this patent, a novel technique was disclosed to expand the spinal canal by lengthening the spinal pedicles on both sides of a vertebra resulting in decompression of compressed nerves while maintaining normal anatomic structures and muscle attachments. This disclosure relies on the same principle, namely that lengthening spinal pedicles can relieve the symptoms of spinal stenosis. This disclosure achieves expansion of the spinal canal by a percutaneous technique, thus eliminating the need for a larger incision.

SUMMARY OF THE INVENTION

In accordance with an aspect of the present invention, there is provided a bone saw. The bone saw includes a flexible saw blade comprising a distal end, a proximal end, and a distal tip comprising a cutting edge. The flexible saw blade is rectangular in shape over at least a portion of a length thereof. The bone saw further includes a saw handle base insert and a saw shaft tip assembly comprising a saw shaft tip comprising a channel comprising a distal end and a proximal end. The saw shaft tip assembly further comprises a saw channel insert disposed within the channel of the saw shaft tip to form a lumen between the saw shift tip and the saw channel insert and an opening through which the flexible saw blade is advanced.

In accordance with another aspect of the present invention, there is provided a bone saw. The bone saw comprises a flexible saw blade comprising a distal end, a proximal end, and a distal tip comprising a cutting edge. The flexible saw blade is rectangular in shape over at least a portion of a length thereof. The bone saw further comprises a saw handle base insert, a saw shaft tip assembly comprising opening through which the flexible saw blade is advanced, and a saw blade advancement mechanism coupled to the flexible saw blade for moving the flexible saw blade in discrete amounts.

BRIEF DESCRIPTION OF THE DRAWINGS

For the purpose of illustration, there are shown in the drawings certain embodiments of the present invention. In the drawings, like numerals indicate like elements throughout. It should be understood that the invention is not limited to the precise arrangements, dimensions, and instruments shown. In the drawings:

FIG. 3A illustrates a side view of the saw handle base insert of FIG. 1E, in accordance with an exemplary embodiment of the present invention;

FIG. 3B illustrates a cross-sectional view of the saw handle base insert of FIG. 1E, in accordance with an exemplary embodiment of the present invention;

FIGS. 4A through 4F illustrate various views of the saw shaft tip of FIG. 1E, in accordance with an exemplary embodiment of the present invention;

DETAILED DESCRIPTION OF THE INVENTION

Figure 1A:
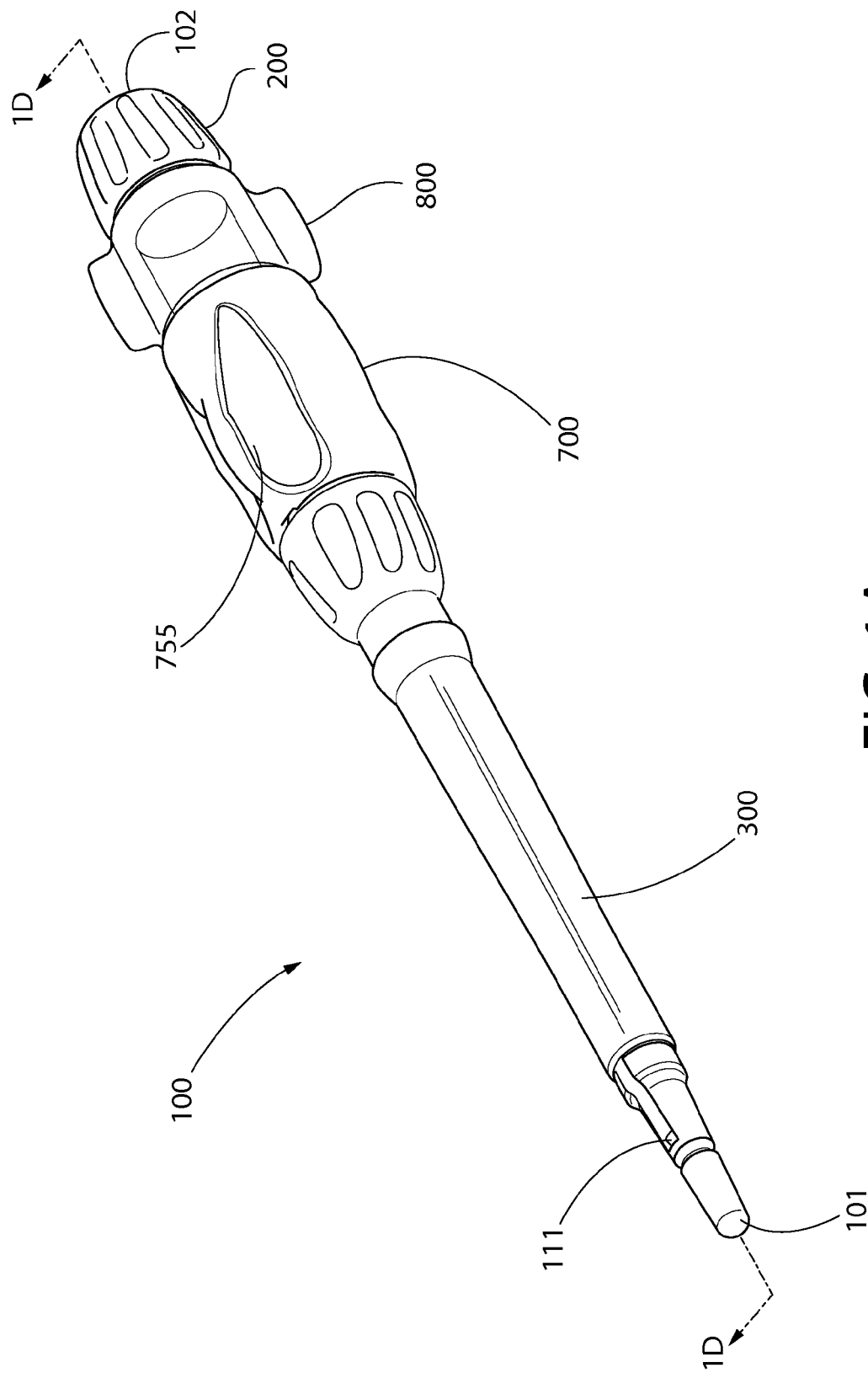
FIG. 1A illustrates a bone saw assembly, in accordance with an exemplary embodiment of the present invention.

Reference to the drawings illustrating various views of exemplary embodiments of the present invention is now made. In the drawings and the description of the drawings herein, certain terminology is used for convenience only and is not to be taken as limiting the embodiments of the present invention. Furthermore, in the drawings and the description below, like numerals indicate like elements throughout.

Figure 1B:
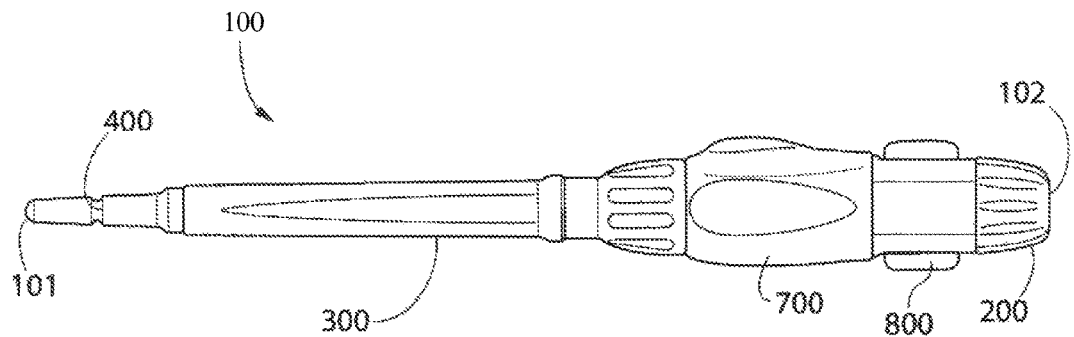
FIG. 1B illustrates a side view of the bone saw assembly of FIG. 1A, in accordance with an exemplary embodiment of the present invention.
Figure 1C:
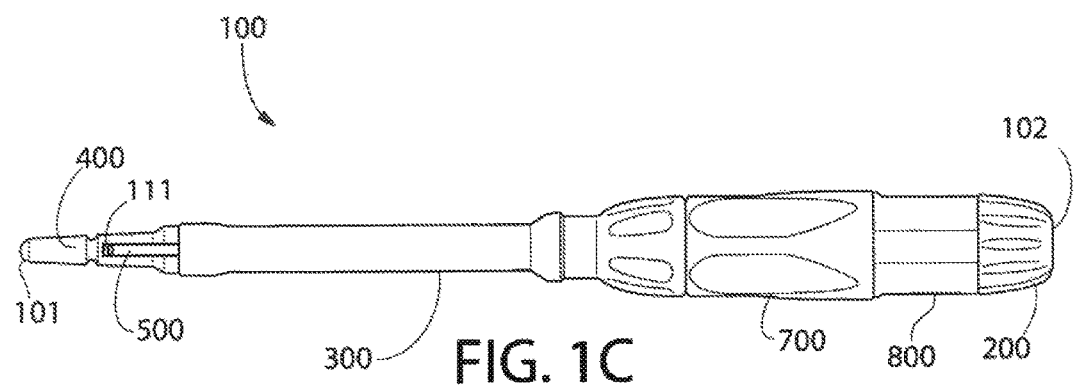
FIG. 1C illustrates a top view of the bone saw assembly of FIG. 1A, in accordance with an exemplary embodiment of the present invention.
Figure 1D:
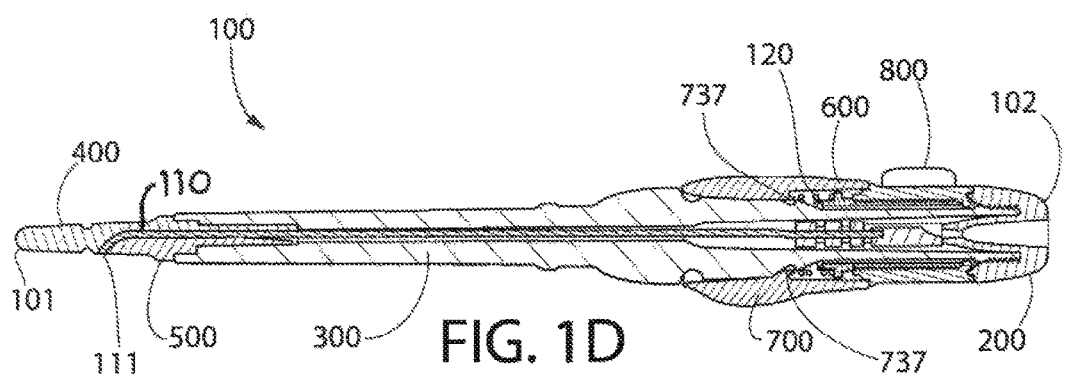
FIG. 1D illustrates a view of a cross section of the bone saw assembly of FIG. 1A, in accordance with an exemplary embodiment of the present invention.
Figure 1E:
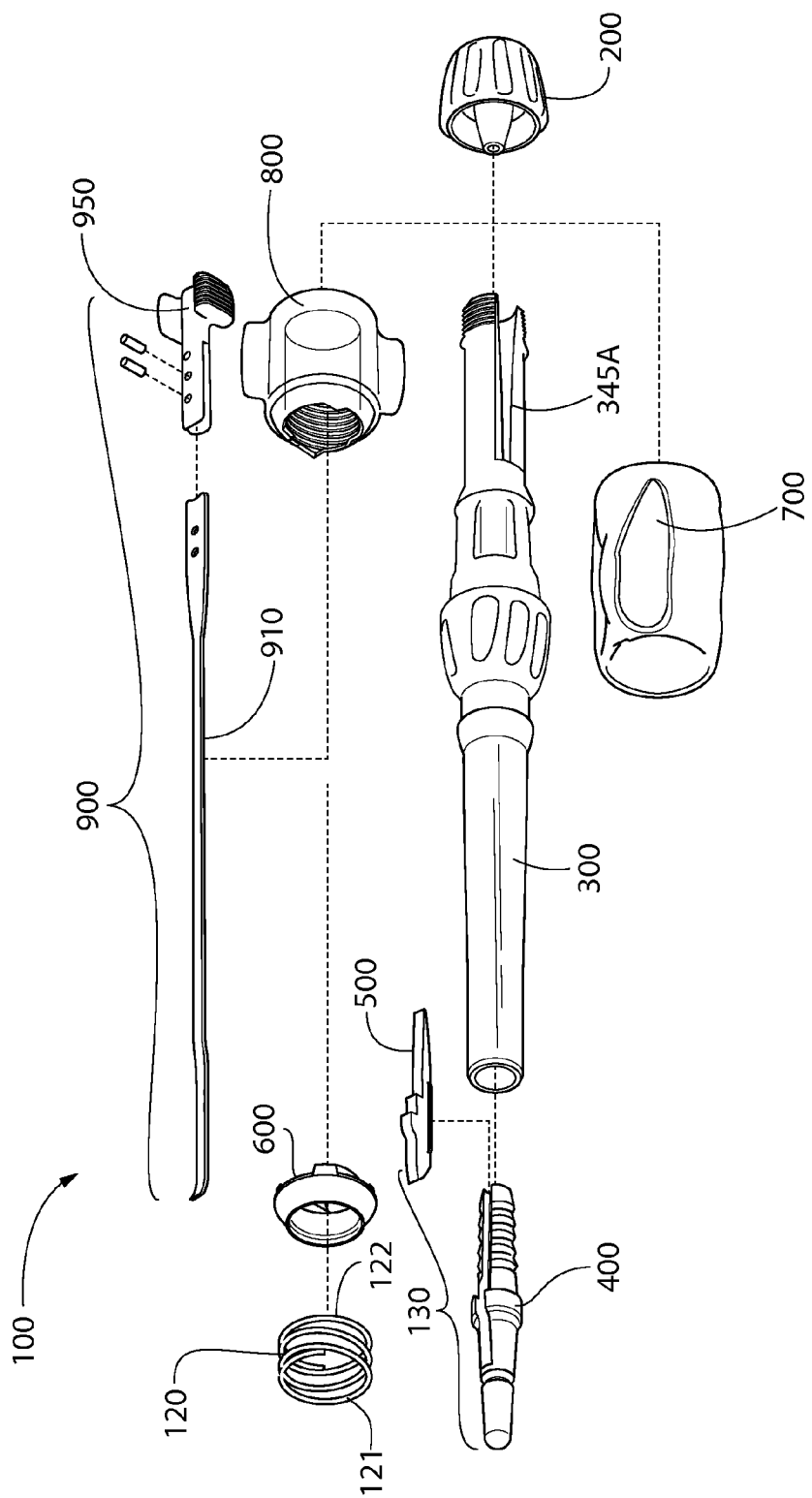
FIG. 1E illustrates an exploded view of the bone saw assembly of FIG. 1A, the bone saw assembly comprising a saw release spring, an end cap, a saw handle base insert, a saw shaft tip assembly comprising a saw shaft tip and a saw channel insert, a spring feedback ring, a saw handle body, a driver collar, and a saw blade assembly, in accordance with an exemplary embodiment of the present invention.

Referring now to FIG. 1A there is illustrated a bone saw assembly (also referred to herein as a "bone saw"), generally designated as 100, in accordance with an exemplary embodiment of the present invention. The bone saw assembly comprises a distal end 101 and a proximal end 102. FIG. 1B illustrates a side view of the bone saw assembly 100; FIG. 1C illustrates a top view of the bone saw assembly 100, FIG. 1D illustrates a view of a cross-section of the bone saw assembly 100 taken along a line 1D-1D in FIG. 1A; and FIG. 1E illustrates an exploded view of the bone saw assembly 100, in accordance with an exemplary embodiment of the present invention.

Referring to FIGS. 1A through 1E, the bone saw assembly comprises a saw release spring 120, an end cap 200, a saw handle base insert 300, a saw shaft tip assembly 130 comprising a saw shaft tip 400 and a saw channel insert 500, a spring feedback ring 600, a saw handle body 700, a driver collar 800, and a saw blade assembly 900. The driver collar 800 is used to advance and retreat the saw blade assembly 900 in discrete amounts via a click action, as described in more detail below.

Figure 2A:
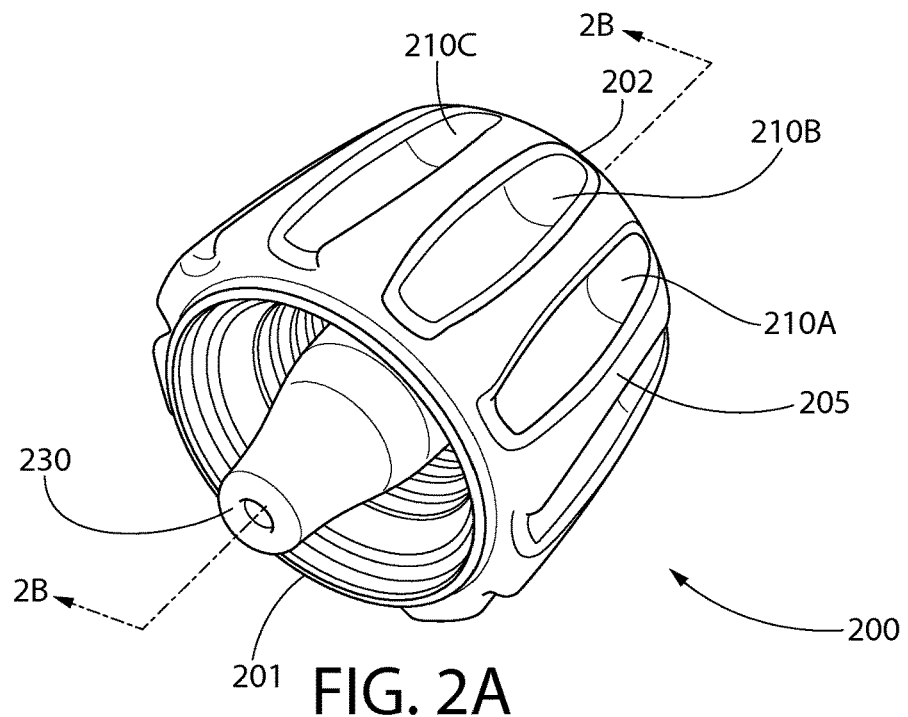
FIG. 2A illustrates a perspective view of the end cap of FIG. 1E, in accordance with an exemplary embodiment of the present invention.
Figure 2B:
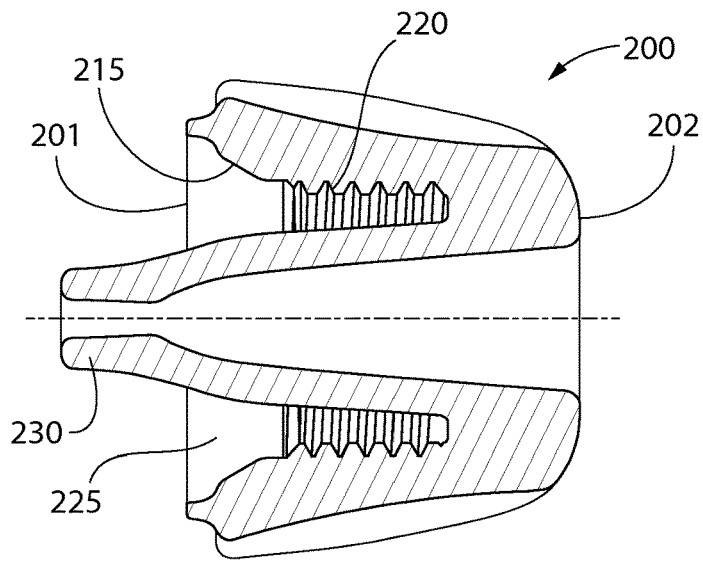
FIG. 2B illustrates a cross sectional view of the end cap of FIG. 1E, in accordance with an exemplary embodiment of the present invention.

Referring to FIG. 2A, there is illustrated a perspective view of the end cap 200, and to FIG. 2B, there is illustrated a view of a cross-section of the end cap 200 taken along a line 2B-2B in FIG. 2A, in accordance with an exemplary embodiment of the present invention. The end cap 200 comprises a distal end 201, a proximal end 202, and a grooved outer wall 205. The grooved outer wall 205 comprises a plurality of grooves 210A, 210B, 210C, etc. to provide a grip so that the end cap 200 can be secured and removed from the bone saw assembly 100.

The end cap 200 further comprises an inner wall 215 comprising threads 220. The end cap 200 is secured to the bone saw assembly 100 and more specifically to the saw handle base insert 300 by the threads 220. Extending distally from an interior cavity 225 of the end cap 200 is a projection 230. The projection 230 acts as a proximal stop for the saw blade assembly 900 to limit its proximal movement.

Referring now to FIG. 3A, there is illustrated a top view of the saw handle base insert 300, and to FIG. 2B, there is illustrated a view of a cross-section of the saw handle base insert 300 taken along a line 3B-3B in FIG. 3A, in accordance with an exemplary embodiment of the present invention. The saw handle base insert 300 has a distal end 301 and a proximal end 302. The saw handle base insert 300 comprises a first gently tapering wall portion 310, a handle wall portion 320, a body wall portion 330, and a split wall portion 340. The body wall portion 330 comprises a circumferential groove or waist 337.

The split wall portion 340 comprises threads 345 thereon at the proximal end 302 of the saw handle base insert 300. The threads 345 are sized to mate with the threads 220 of the end cap 200 to secure the end cap 200 to the proximal end 302 of the saw handle base insert 300. A perpendicular cross section of the split wall portion 340 has a stadium shape (ignoring the illustrated split).

The saw handle base insert 300 further comprises an interior lumen 350 comprising three main portions: a distal cavity 360 at the distal end 301 of the saw handle base insert 300, a proximal cavity 380 at the proximal end 302 of the saw handle base insert 300, and a central lumen 370 extending from the distal cavity 360 to the proximal cavity 380 along a central longitudinal axis to form the interior lumen 350.

Figure 4A:
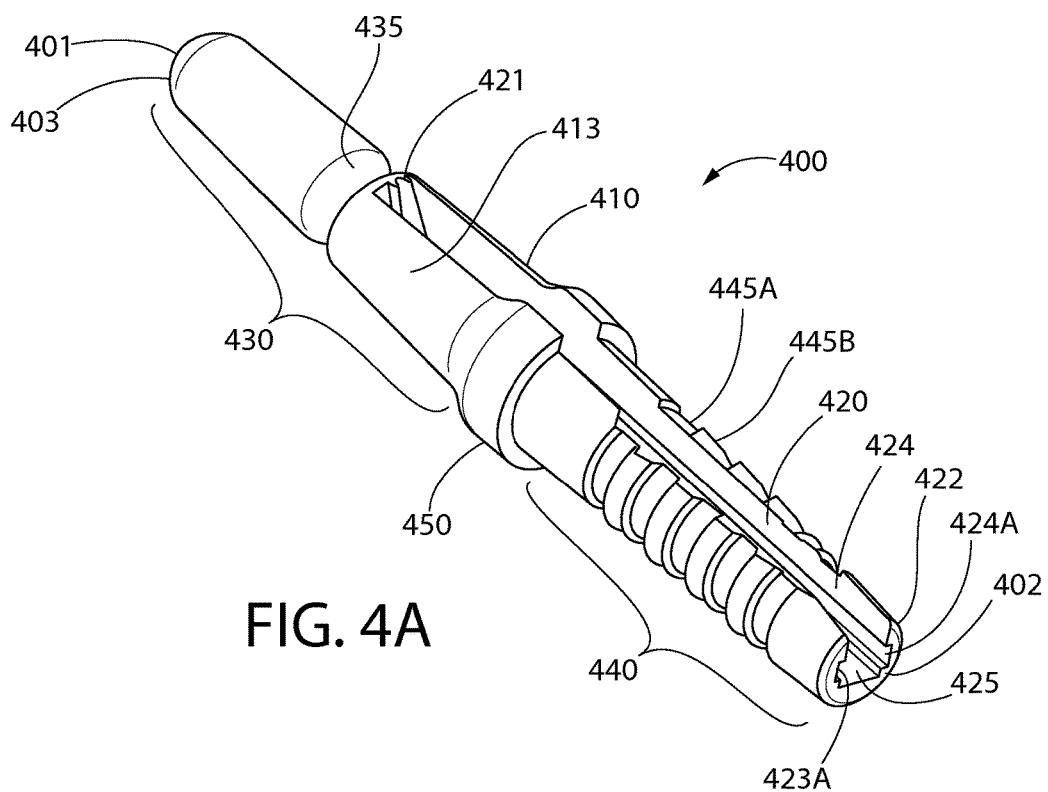
Figure 4B:
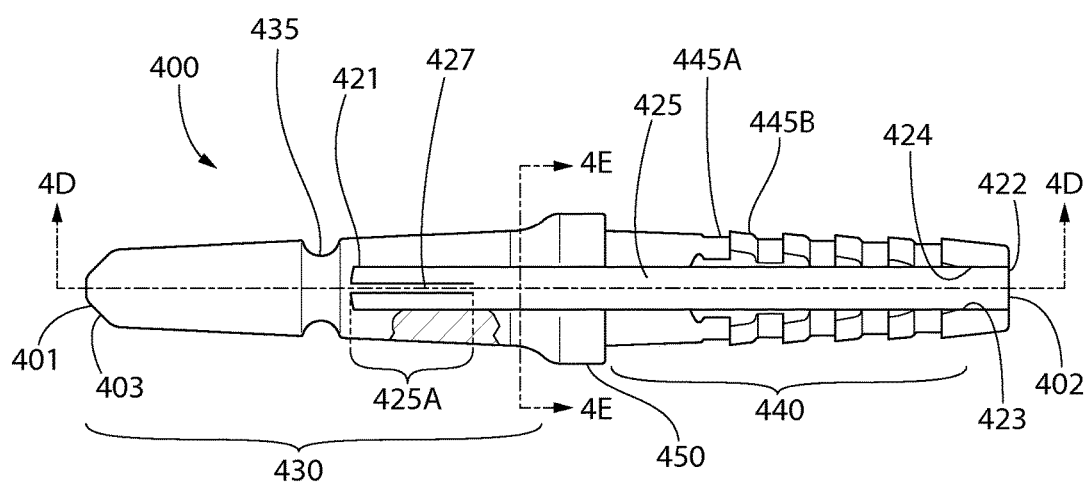
Figure 4E:
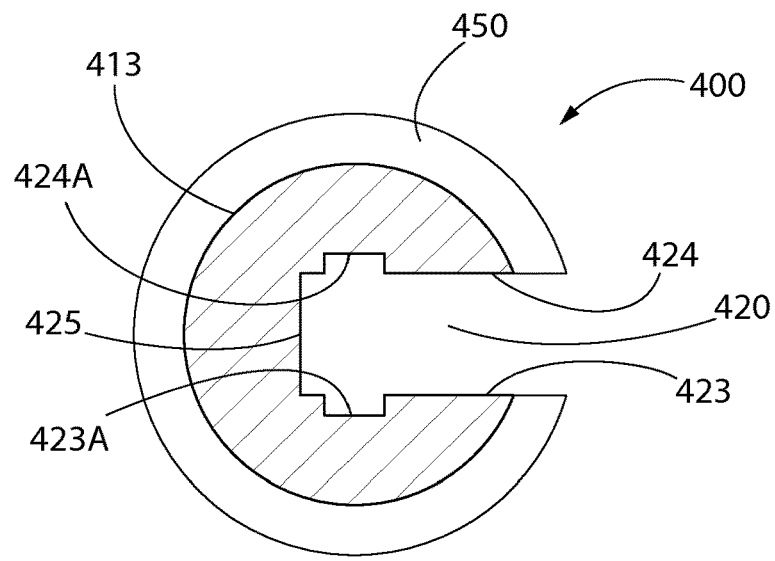
Figure 4F:
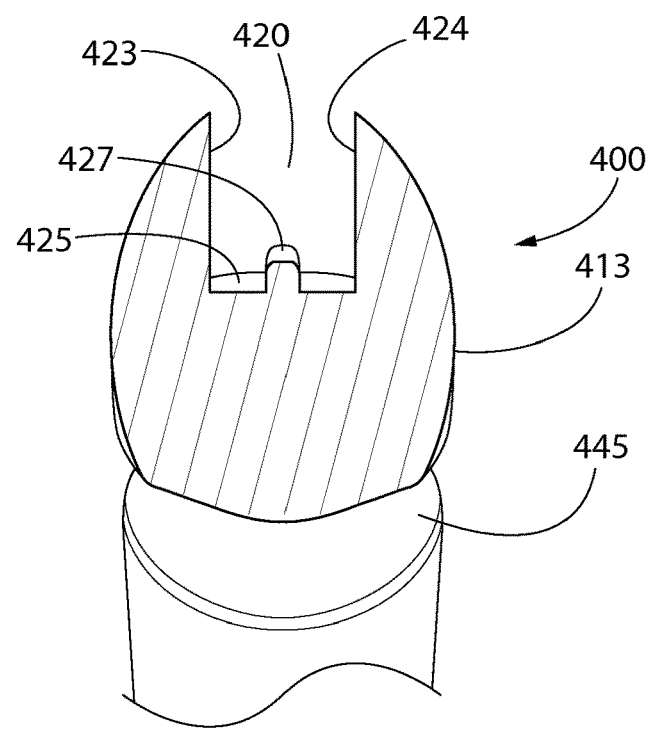

Illustrated in FIGS. 4A through 4F are various views of the saw shaft tip 400, in accordance with an exemplary embodiment of the present invention. FIG. 4A illustrates a perspective view of the saw shaft tip 400. FIG. 4B illustrates a top view of the saw shaft tip 400. FIG. 4C illustrates a side view of the saw shaft tip 400. FIG. 4D illustrates a view of a cross section of the saw shaft tip 400 taken along a line 4D-4D in FIG. 4B. FIG. 4E illustrates a view of a cross section of the saw shaft tip 400 taken along a line 4E-4E in FIG. 4B. FIG. 4F illustrates a view of a cross section of the saw shaft tip 400 taken along a line 4F-4F in FIG. 4D.

Referring now to FIGS. 4A through 4F together, the saw shaft tip 400 has a distal end 401 and a proximal end 402. The saw shaft tip 400 comprises a body 410 comprising an outer surface 413. The saw shaft tip 400 further comprises a channel 420 disposed within the body 410. The channel 420 has a distal end 421 and a proximal end 422. The proximal end 422 of the channel 420 is located at the proximal end 402 of the saw shaft tip 400. The channel 420 is open at its proximal end 422. Located at the distal end 401 of the saw shaft tip 400 is a trunnion 403 which is used for aligning the distal end 401 of the saw shaft tip 400.

The channel 420 extends from the proximal end 402 toward the distal end 401 of the saw shaft tip 400 but terminates before the distal end 401 of the saw shaft tip 400. The channel 420 comprises a first side wall 423 in which a longitudinal slot or channel 423A is formed and a second side wall 424 in which a longitudinal slot or channel 424A is formed.

The channel 420 further comprises a floor 425 which extends from the proximal end 422 of the channel 420 to the distal end 421 of the channel 420. At the distal end 421 of the channel 420, the floor 425 curves upwardly to the outer surface 413 of the body 410 of the saw shaft tip 400. The floor 425 meets the outer surface 413 of the body 410 at the distal end 421 of the channel 420.

The floor 425 curves between a point 428 in the channel 420 near the distal end 421 of the channel 420 and the distal end 421 of the channel 420. Disposed on the curved portion of the floor 425 in a longitudinal direction, which curved portion is designated in FIG. 4D as 425A, is a curved ridge or abutment 427. Because the abutment 427 is longitudinally disposed on the curved portion 425A, the abutment 427 is longitudinally curved. The curved portion 425A of the floor 425 urges a distal dip of the saw blade assembly 900 to curve, as more fully described below.

The longitudinal channel 423A spans the first side wall 423 in a longitudinal direction from the proximal end 402 of the saw shaft tip 400 to about the point 428 of the channel 420. Likewise, the longitudinal channel 424A spans the second side wall 424 in a longitudinal direction from the proximal end 402 of the saw shaft tip 400 to about the point 428 of the channel 420.

The body 410 of the saw shaft tip 400 comprises three sections: a distal tip section 430, a proximal tip section 440, and a bulged waist section 450. The distal tip section 430 tapers inwardly from the bulged waist section 450 toward the distal end 401 of the saw shaft tip 400. Disposed in the outer wall 413 in the distal tip section 430 is a circumferential groove 435. The circumferential groove 435 is a radiographic marker that is located a same distance from the distal tip 101 of the bone saw assembly 100 as similar radiographic markers on related surgical instruments, such as those in the kit assembly 1100 described below. The radiographic marker 435 ensures proper depth of insertion of the bone saw assembly 100 and use in a pedicle of a patient. The radiographic marker 435 is positioned for location at a base of the pedicle (e.g., at a junction of the pedicle and vertebral body) in the pedicle passage, described in more detail below.

The proximal tip section 440 tapers inwardly from the bulged waist section 450 toward the proximal end 402 of the saw shaft tip 400. Disposed in the outer wall 413 in the proximal tip section 440 is a plurality of circumferential grooves 445A and circumferential teeth 445B. The bulged waist section 450 comprises a tapered distal surface 451 and a proximal edge 452.

The outer wall 413 in the proximal tip section 440 is sized to be press-fit into the distal cavity 360 of the saw handle base insert 300 and firmly retained therein. The circumferential teeth 445B grip an interior surface of the distal cavity 360. When so disposed, the proximal edge 452 of the bulged waist section 450 abuts the distal end 301 of the saw handle base insert 300.

In an exemplary embodiment, the saw shaft tip 400 is metal, and the saw handle base insert 300 is plastic. In such embodiment, the teeth 445B of the saw shaft tip 400 are metal and cut into the interior surface of the distal cavity 360 to firmly retain the proximal tip section 440 with the distal cavity 360 of the saw handle base insert 300.

Figure 5A:
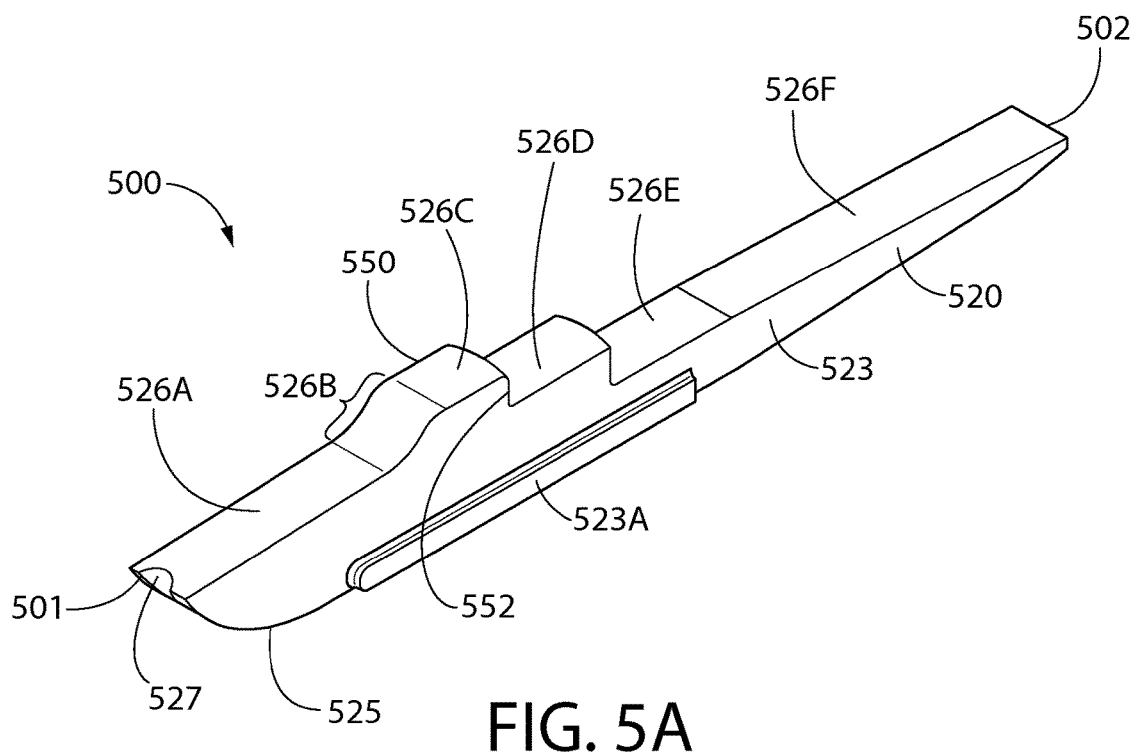
FIGS. 5A through 5E illustrate various views of the saw channel insert of FIG. 1E, in accordance with an exemplary embodiment of the present invention.
Figure 5B:
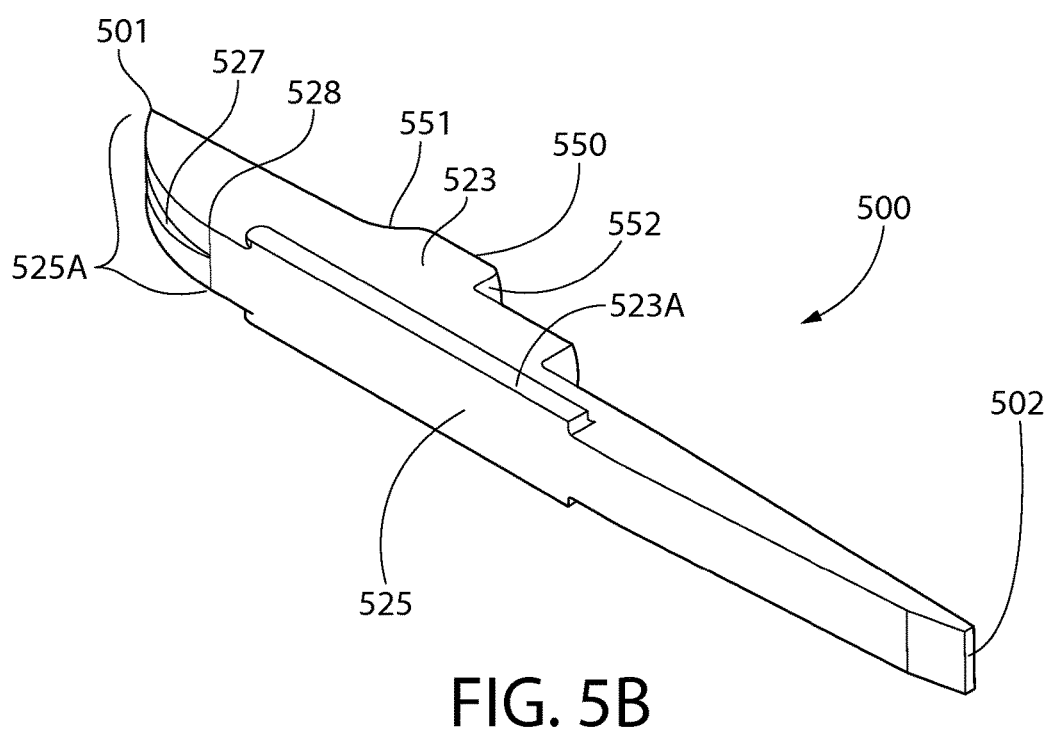
Figure 5C:
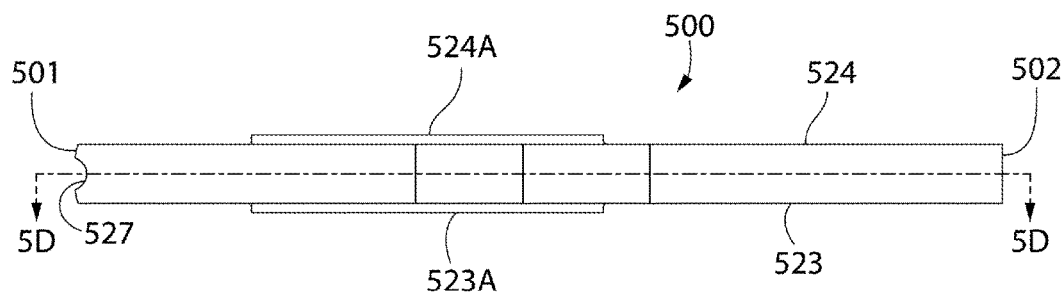
Figure 5D:
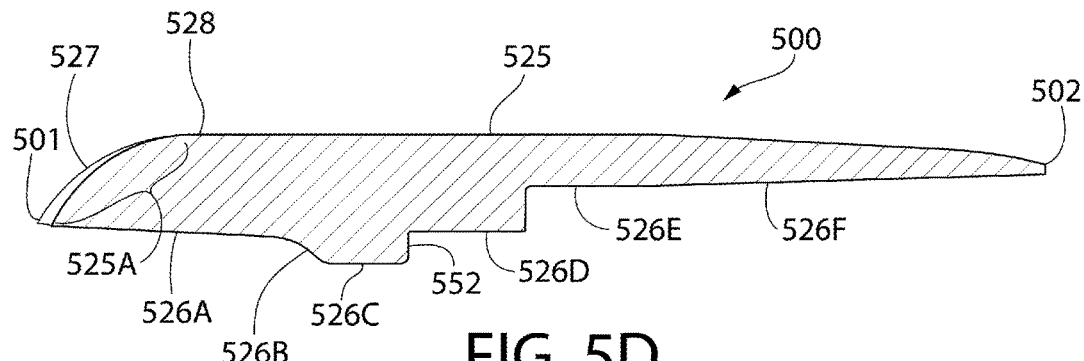
Figure 5E:
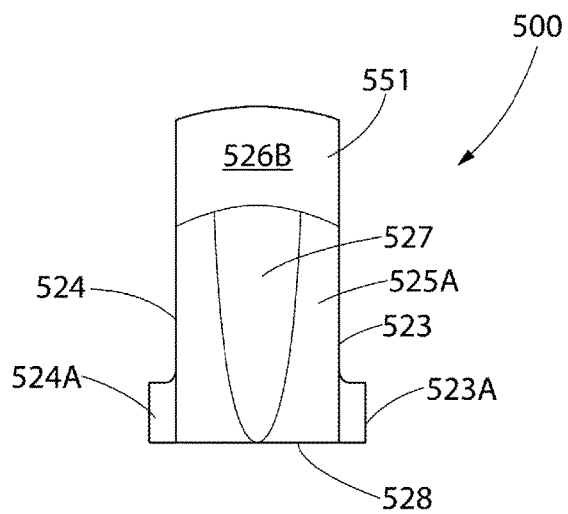

Illustrated in FIGS. 5A through 5E are various views of the saw channel insert 500, in accordance with an exemplary embodiment of the present invention. FIG. 5A illustrates a top perspective view of the saw channel insert 500. FIG. 5B illustrates a bottom perspective view of the saw channel insert 500. FIG. 5C illustrates a top view of the saw channel insert 500. FIG. 5D illustrates a view of a cross section of the saw channel insert 500 taken along a line 5D-5D in FIG. 5C. FIG. 5E illustrates a distal end view of the saw channel insert 500.

Referring now to FIGS. 5A through 5E together, the saw channel insert 500 has a distal end 501 and a proximal end 502. The saw channel insert 500 comprises a body 520 comprising an outer surface.

The body 520 extends from the distal end 501 to the proximal end 502 of the saw channel insert 500. The body 520 comprises a first side wall 523 on which a longitudinal ridge 523A is formed and a second side wall 524 on which a longitudinal ridge 524A is formed.

The body 520 further comprises a bottom surface 525 which extends from the distal end 501 to the proximal end 502 of the saw channel insert 500. The body 520 further comprises a top surface 526, which comprises portions 526A through 526F. At the distal end 501 of the saw channel insert 500, the bottom surface 525 curves upwardly to the portion 526A of the top surface 526. The bottom surface 525 meets the portion 526A of the top surface 526 at the distal end 501 of the saw channel insert 500.

The bottom surface 525 curves between a point 528 on the bottom surface 525 near the distal end 501 of the saw channel insert 500 and the distal end 501 of the saw channel insert 500. Disposed on the curved portion of the bottom surface 525 in a longitudinal direction, which curved portion is designated in FIG. 5B as 525A. Because the groove 527 is longitudinally disposed on the curved portion 525A, the groove 527 is longitudinally curved to complement the longitudinally curved abutment 427.

The longitudinal ridge 523A spans the first side wall 523 in a longitudinal direction from approximately the point 528 to a point between the midpoint of the saw channel insert 500 and the proximal end 502 of the saw channel insert 500. Likewise, the longitudinal ridge 524A spans the second side wall 524 in a longitudinal direction from approximately the point 528 to a point between the midpoint of the saw channel insert 500 and the proximal end 502 of the saw channel insert 500.

As discussed above, the top surface 526 of the body 520 comprises portions 526A through 526F. The portion 526A is curve to match a radius of curvature of the saw shaft tip 400 in the distal tip section 430. The portions 526B and 526C form a bulged waist portion 550, which further comprises a proximal edge 552. The portion 526D is stepped down from the portion 526C, and the portion 526E is stepped down from the portion 526D. The portion 526F tappers inwardly toward the proximal end 502.

The ridges 523A and 524A of the saw channel insert 500 are sized to fit within the respective channels 423A and 423A of the saw shaft tip 400. When so disposed, the ridge 427 of the saw shaft tip 400 complements the groove 527 of the saw channel insert 500. When assembled, the saw channel insert 500 is sized to provide a channel or lumen 110 (illustrated in FIG. 1D) between the saw shaft tip 400 and the saw channel insert 500. The lumen 110 extends from the proximal ends of the saw shaft tip 400 and the saw channel insert 500 in the channel 420 of the saw channel insert 500 between the floor 425 of the channel 420 and the bottom surface 525 of the saw channel insert 500 to the distal end 421 of the channel 420 and the distal end 501 of the saw channel insert 500, where the lumen 110 is open. When the saw channel insert 500 is disposed within the saw shaft tip 400 and the assembly 120 is attached to the saw handle base insert 300, as illustrated in FIGS. 1A through 1D, the lumen 110 opens to the outside of the bone saw assembly 100 via an opening 111. In an exemplary embodiment, the saw channel insert 500 is metal, and the saw handle base insert is plastic.

Referring again to FIGS. 1A, 1E, and 3A, the spring 120 is disposed about the body wall portion 330 of the handle base insert 300. The spring 120 has a distal end 121 and a proximal end 122. The handle wall portion 320 of the handle base insert 300 further comprises an annular ledge 322 against which the distal end 121 of the spring 120 abuts when disposed about the body wall portion 330 of the handle base insert 300.

Figure 6A:
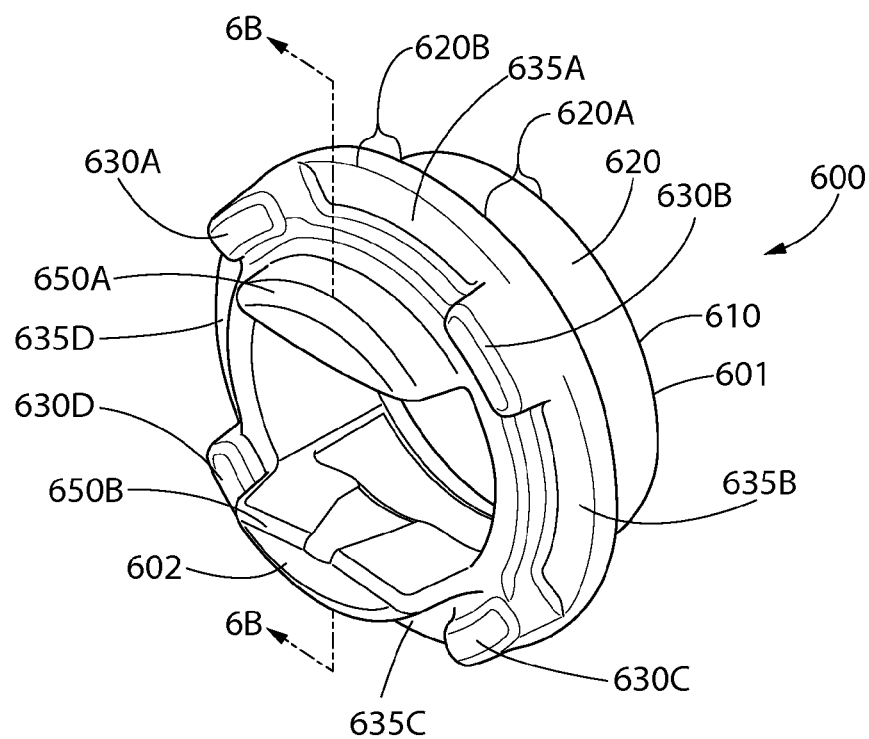
FIG. 6A illustrates a perspective view of the spring feedback ring of FIG. 1E, in accordance with an exemplary embodiment of the present invention.
Figure 6B:
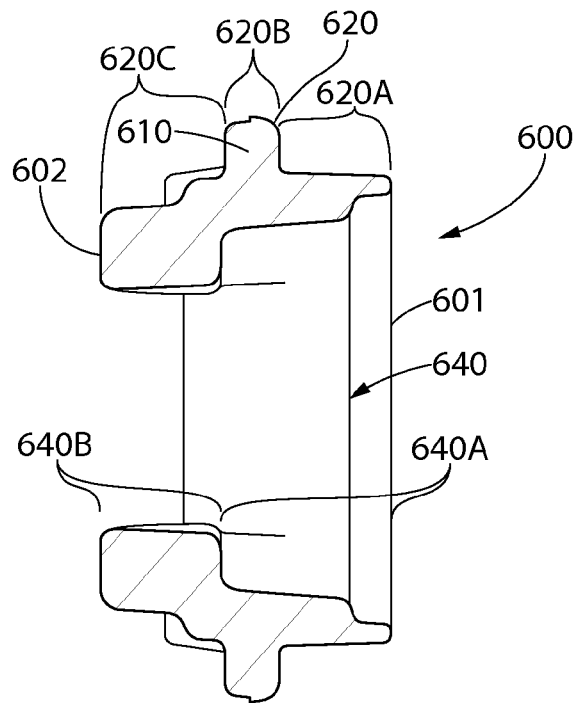
FIG. 6B illustrates a cross-sectional view of the spring feedback ring of FIG. 1E, in accordance with an exemplary embodiment of the present invention.

Illustrated in FIG. 6A is a perspective view of the spring feedback ring 600. Illustrated in FIG. 6B is a view of a cross section of the spring feedback ring 600 taken along a line 6C-6C in FIG. 6A. Illustrated in FIG. 6C is a side view of the spring feedback ring 600.

Figure 6C:
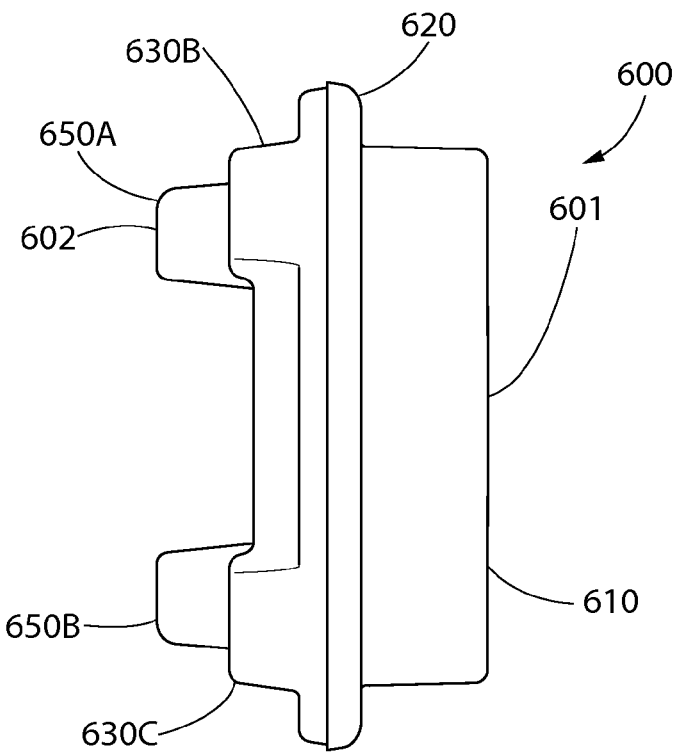
FIG. 6C illustrates a side view of the spring feedback ring of FIG. 1E, in accordance with an exemplary embodiment of the present invention.

With reference to FIGS. 6A through 6C, the spring feedback ring 600 has a distal end 601 and a proximal end 602. The spring feedback ring 600 comprises a body 610 comprising an outer wall 620 comprising three portions: a distal portion 620A, a proximal portion 620C, and a middle portion 620B. The distal portion 620A is cylindrically shaped and is sized to be snuggly fit within the proximal end 122 of the spring 120. The proximal portion 520C comprises a plurality of teeth 630A, 630B, 630C, and 630D interspersed with gaps 635A, 635B, 635C, and 635D. The proximal portion 620C further comprises a pair of projections 650A and 650B extending proximally.

The body 610 forms an interior cavity 640 comprising a distal portion 640A and a proximal portion 640B. The distal portion 640A is generally cylindrically shaped, and the proximal portion 640B has a stadium shape to be disposed about the split wall portion 340 of the handle base insert 300. The projections 650A and 650B increase the depth of the proximal portion 640B of the interior cavity 640.

As mentioned above, the feedback ring 600 is disposed about the split wall portion 340 of the handle base insert 300. The distal portion 620A of the feedback ring 600 is snuggly fit within the proximal end 122 of the spring 120 when so disposed. The feedback ring 600 and the spring 120 are disposed within the saw handle body 700.

Figure 7:
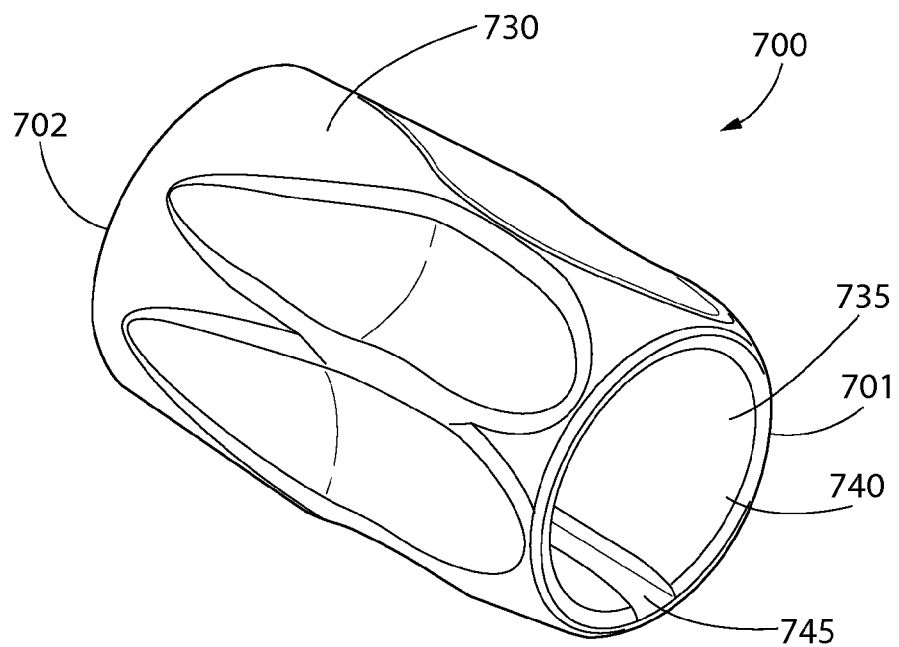
FIG. 7 illustrates a perspective view of the saw handle body of FIG. 1E, in accordance with an exemplary embodiment of the present invention.

Referring now to FIG. 7, there is illustrated a perspective view of the saw handle body 700, in accordance with an exemplary embodiment of the present invention. The saw handle body 700 has a distal end 701 and a proximal end 702. The saw handle body 700 comprises a wall 730 defining an interior cavity 740 extending from the distal end 701 to the proximal end 702. The wall 730 comprises a ridge 755 (illustrated in FIG. 1A) that is aligned with the opening 111. The ridge 737 allows a surgeon to know the rotational location of the opening 111 when using the bone saw assembly 100.

Disposed on an inside surface 735 of the outer wall 730 is a channel 745, which spans the length of the saw handle body 700 longitudinally from the distal end 701 to the proximal end 702. The feedback ring 600 and the spring 120 are disposed within the saw handle body 700, as seen in FIG. 1D. Extending from the inside surface 735 of the outer wall 730 are one or more projections 737 (illustrated in FIG. 1D), which engage with the circumferential groove or waist 337 of the handle base insert 300.

Figure 8A:
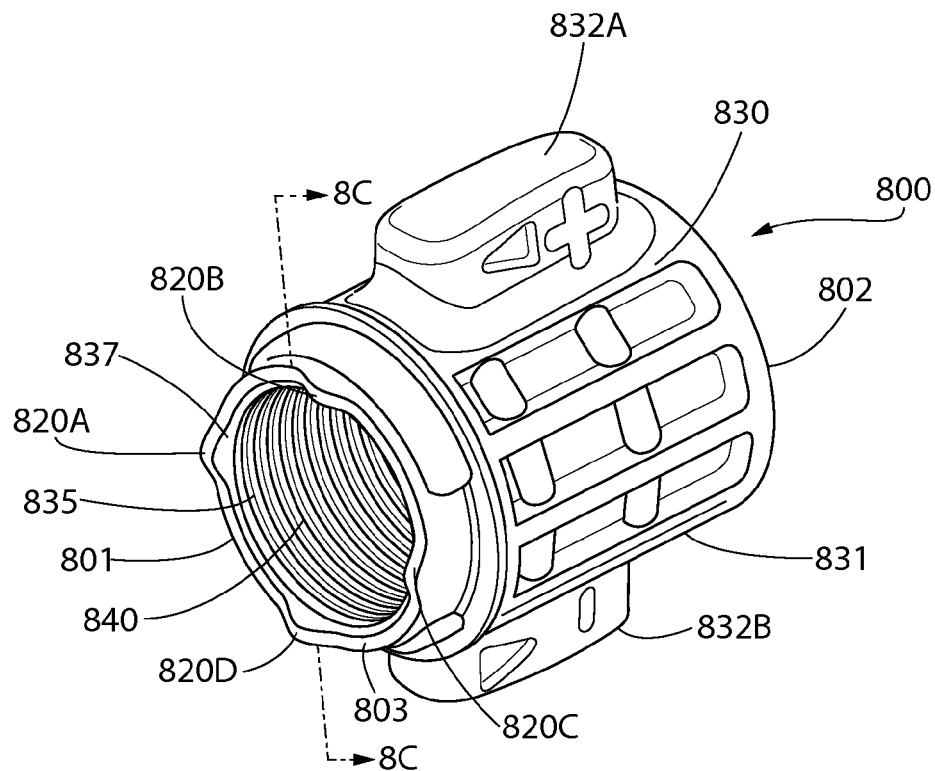
FIG. 8A illustrates a perspective view of the driver collar of FIG. 1E, in accordance with an exemplary embodiment of the present invention.
Figure 8B:
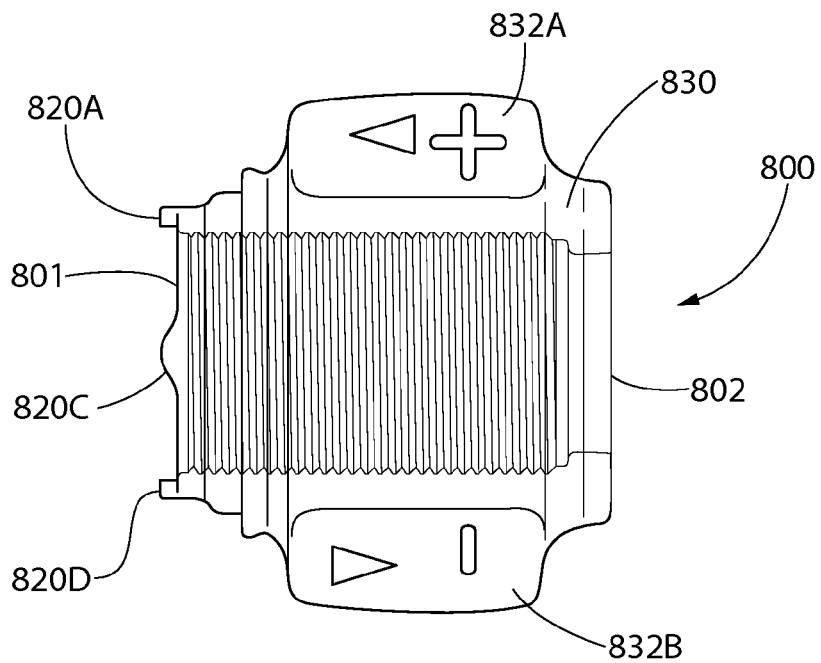
FIG. 8B illustrates a side view of the driver collar of FIG. 1E, in accordance with an exemplary embodiment of the present invention.
Figure 8C:
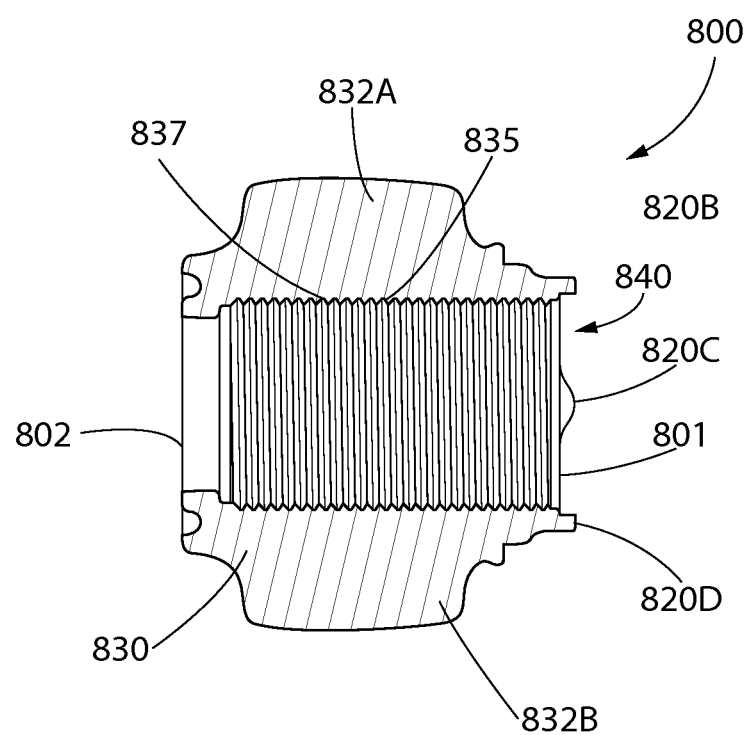
FIG. 8C illustrates a cross-sectional view of the driver collar of FIG. 1E, in accordance with an exemplary embodiment of the present invention.

Illustrated in FIG. 8A is a perspective view of the driver collar 800, in accordance with an exemplary embodiment of the present invention. FIG. 8B illustrates a side view of the driver collar 800, and FIG. 8C illustrates a view of a cross section of the driver collar 800 taken along a line 8C-8C in FIG. 8A. The driver collar 800 has a distal end 801 and a proximal end 802. The driver collar 800 comprises a wall 830 defining an interior cavity 840 extending from the distal end 801 to the proximal end 802. Disposed on an outside surface 831 of the wall 830 is a pair of handles 832A and 832B that provide press surfaces so that the driver collar 800 may be rotated during use by a surgeon. Disposed on an inside surface 835 are threads 837.

Formed by the wall 830 at the distal end 801 of the driver collar 800 are a plurality of distally projecting teeth 820A, 820B, 820C, and 820D. The teeth 820A through 820D are circumferentially spaced from one another about a distal opening 803 of the driver collar 800. The teeth 820A through 820D are circumferentially spaced to alternately be in contact with the teeth 630A through 630D of the feedback ring 600 and the gaps 635A through 635D of the feedback ring 600.

When assembled into the bone saw assembly 100, the distal end 801 of the driver collar 800 abuts the proximal end 602 of the feedback ring 600. The teeth 820A through 820D are disposed within respective ones of the gaps 635A through 635D of the feedback ring 600. The spring 120 urges the feedback ring 600 toward the collar 800 and causes the feedback ring 600 to resist rotation of the collar 800. As the collar 800 is turned by a surgeon, the teeth 820A through 820D come into contact with the teeth 630A through 630D. Because the spring 120 urges the feedback ring 600 toward the collar 800, the teeth 630A through 630D oppose rotation of the teeth 820A through 820D. The teeth 820A through 820D, however, are rounded and pass over the teeth 630A through 630D if sufficient torque is applied to the driver collar 800. If enough torque is provided, the teeth 820A through 820D pass over the teeth 630A through 630D and snap into the gaps 635A through 635D.

Figure 9:
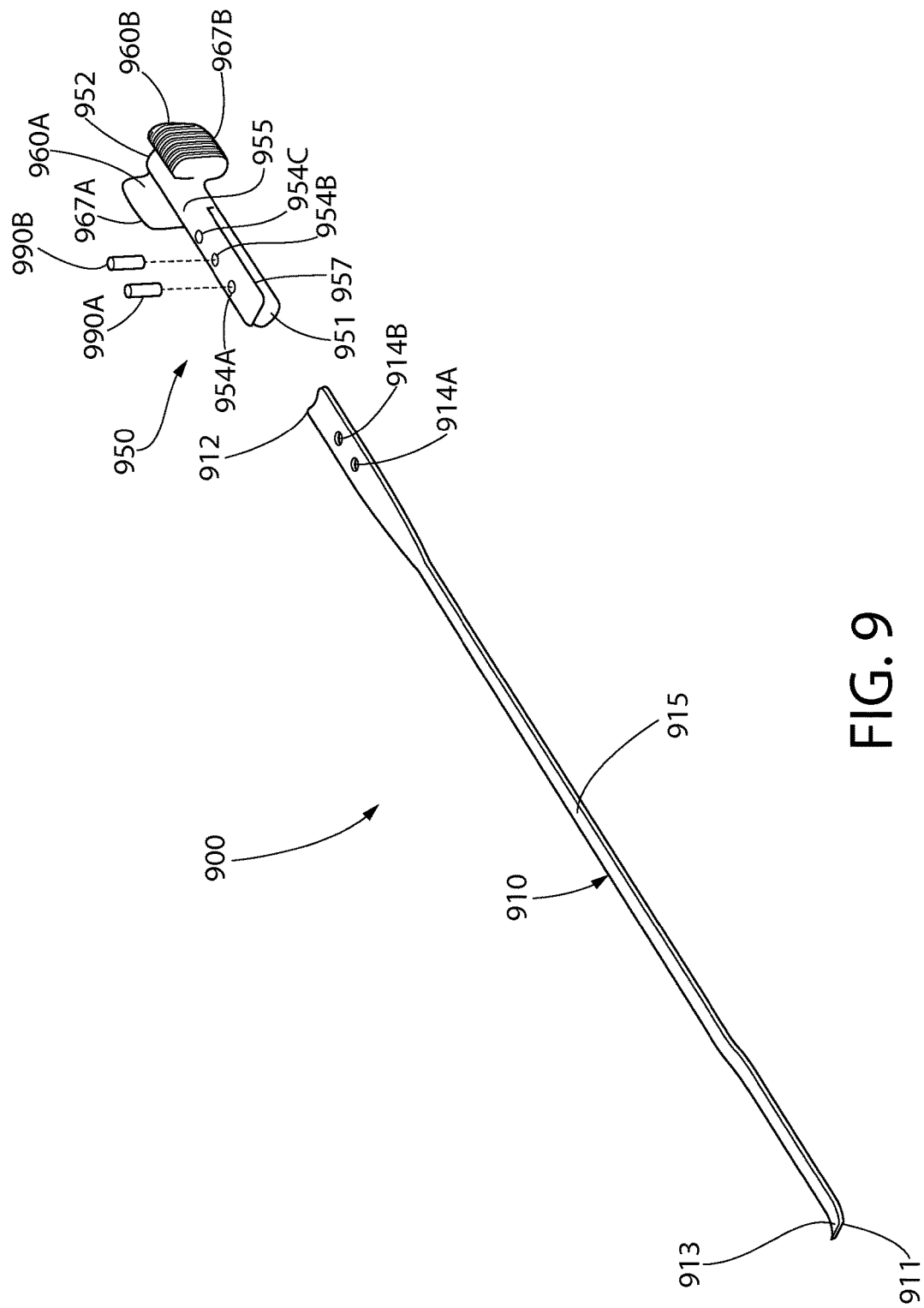
FIG. 9 illustrates an exploded view of the saw blade assembly of FIG. 1E, in accordance with an exemplary embodiment of the present invention.

Referring again to FIG. 1E and also now to FIG. 9, there is illustrated the saw blade assembly 900, which comprises a flexible saw blade 910 and a saw blade driver 950. The saw blade 910 has a distal end 911 and a proximal end 912. The saw blade 910 comprises an elongated, generally rectangular body 915, a curved distal tip 913 at the distal end 911, and two holes 914A and 914B at the proximal end 912. The curvature of the curved distal tip 913 approximately matches that of the curvature of the floor 425 of the channel 420 of the saw shaft tip 400 in the portion 425A. The curved distal tip 913 comprises a cutting edge for cutting bone in human vertebrae.

The saw blade driver 950 has a distal end 951 and a proximal end 952. The saw blade driver 950 comprises a slotted shaft 955 comprising a distal slot 957 and a plurality of distal holes 954A, 954B, and 954C. The saw blade driver 950 further comprises a pair of wings 960A and 960B located at the proximal end 952 of the saw blade driver 950. Disposed on an outer surface 965A and 965B of the respective wings 960A and 960B are respective threads 967A and 967B. The wings 960A and 960B are sized to fit within a circle that has a diameter slightly less than a diameter of the interior cavity 840 of the driver collar 800. The threads 967A and 967B of respective wings 960A and 960B are sized to engage with the threads 837 on the inside surface 835 of the driver collar 800. In an exemplary embodiment, the threads 967A and 967B and the threads 837 are left-hand threads. Other embodiments in which such threads are right-hand threads are contemplated.

The proximal end 912 of the saw blade 910 is sized to fit within the slot 957 of the saw blade driver 950. A pair of pins 990A and 990B are pressed through two of the holes 954A, 954B, and 954C and through the holes 914A and 914B to secure the proximal end 912 of the saw blade 910 to the saw blade driver 950.

The shaft 955 of the saw blade driver 950 is sized to fit within the proximal cavity 380 of the saw handle base insert 300. The wings 960A and 960B are sized to project through respective slots 345A and 345B of the spilt wall portion 340 of the saw handle base insert 300. The saw blade 910 is sized to be disposed within the interior lumen 350, more specifically within the lumen 370, of the saw handle base insert 300 and the lumen 110 of the saw shaft tip assembly 120.

The wings 960A and 960B move longitudinally in the slots 345A and 345B to longitudinally extend or retract the saw blade assembly 900. Longitudinal extension of the saw blade assembly 900 causes translation of the distal tip 913 of the saw blade 910 out of the opening 111 of the lumen 110. Longitudinal retraction of the saw blade assembly 900 causes translation of the distal tip 913 of the saw blade 910 into the opening 111 of the lumen 110.

The longitudinally curved abutment 427 and its complementarily longitudinally curved groove 527 cause the tip 913 of the saw blade 910 to bend concavely as it is translated out of the opening 111. The concave shape imparted to the tip 913 increases its structural rigidity, which assists in sawing bone in vertebrae.

Longitudinal extension and refraction of the saw blade assembly 900 along a longitudinal axis thereof is achieved through rotation of the driver collar 800. As the driver collar 800 is rotated, the threads 837 on the inside surface 835 turn with respect to the threads 967A and 967B of respective wings 960A and 960B because the saw blade driver 950 is prevented from rotating on account of the wings 960A and 960B being disposed within the respective slots 345A and 345B. Thus, as the driver collar 800 is rotated, the saw blade driver 950 is threaded proximally or distally relative to the driver collar 800 depending on the direction of rotation of the driver collar 800.

In the exemplary embodiment illustrated in figures, clockwise rotation of the driver collar 800 when viewed from the proximal end 102 of the bone saw assembly 100 causes the saw blade driver 950 to be threaded distally relative to the driver collar 800. Thus, the saw blade assembly 900 moves distally so that the tip 913 moves out of or further out of the opening 111 generally perpendicularly to the longitudinal axis of the bone saw assembly 100. On the other hand, counterclockwise rotation of the driver collar 800 causes the saw blade driver 950 to be threaded proximally relative to the driver collar 800. Thus, the saw blade assembly 900 moves proximally so that the tip 913 moves into or further into the opening 111. In other embodiments, the directions of rotations of the driver collar 800 may be reversed.

The engagement of the teeth 820A through 820D of the driver collar 800 alternatively with the teeth 630A through 630D and the gaps 635A through 635D of the spring feedback ring 600 provides for tactile feedback for the surgeon when rotating the driver collar 800. Rotation of the driver collar 800 is felt as a series of clicks as it is rotated. The alternative engagement of the teeth 820A through 820D with the teeth 630A through 630D and the gaps 635A through 635D also provides for increased accuracy of the extension and retraction of the tip 913 of the saw blade 910 as each click corresponds to a discrete amount of extension or retraction of the tip 913 of the saw blade 910. The discrete amount of extension or retraction of the tip 913 of the saw blade 910 is determined by the number of teeth 820A through 820D (which matches the number of teeth 630A through 630D) and the pitch of the threads 837 (which matches the pitch of the threads 967A and 967B). The driver collar 800 and the spring feedback ring 600 thereby form a saw blade advancement and retraction mechanism.

Figure 10:
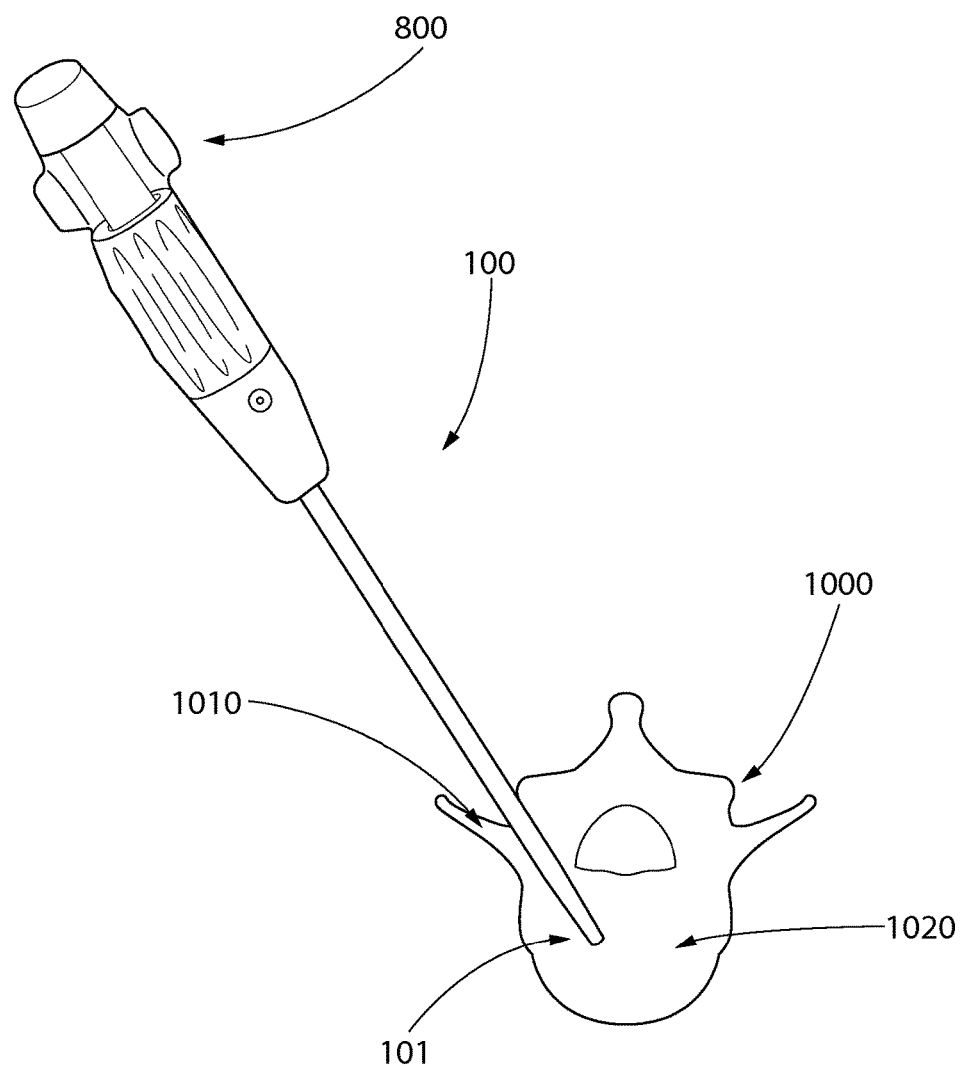
FIG. 10 illustrates an exemplary use of the bone saw assembly of FIG. 1A, in accordance with an exemplary embodiment of the present invention.

Referring now to FIG. 10, there is illustrated an exemplary use of the bone saw assembly 100, in accordance with an exemplary embodiment of the present invention. FIG. 10 illustrates the distal tip 101 of the bone saw assembly 100 inserted into a pedicle 1010 and a vertebral body 1020 of a patient 1000 for making a necessary cut for pedicle lengthening. The tip 913 is located in the pedicle 1010 for cutting the pedicle 1010. The tip 913 may be advanced from the opening 111 by rotating the driver collar 800. The entire bone saw assembly 100 is rotated to cut the pedicle 1010 as one step in a pedicle lengthening process, such as that described in U.S. Pat. No. 8,956,459 issued Feb. 17, 2015, the contents of which are incorporated herein in their entirety by this reference.

Figure 11A:
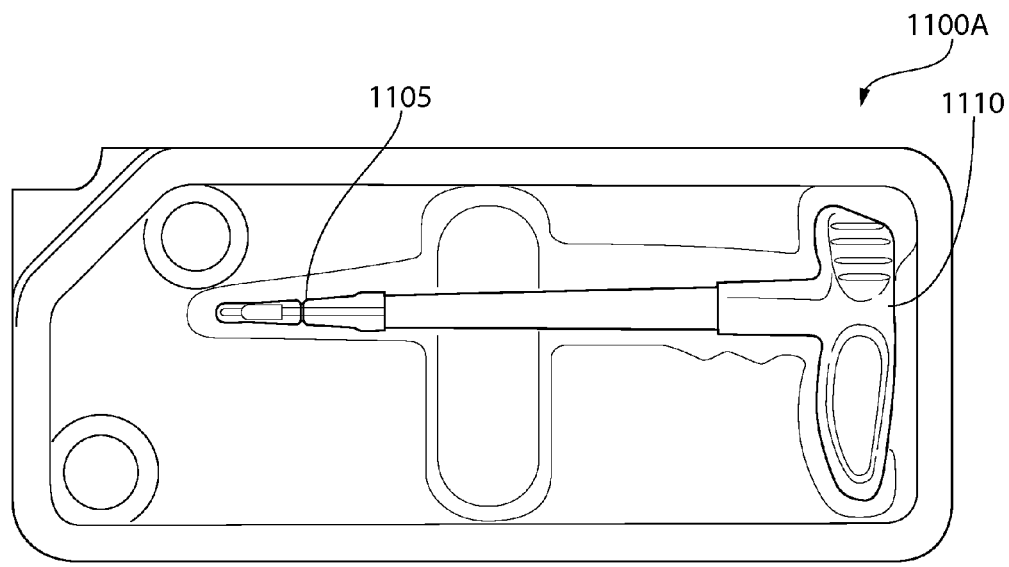
FIGS. 11A through 11C illustrate components of a kit including the bone saw assembly of FIG. 1A, in accordance with an exemplary embodiment of the present invention.
Figure 11B:
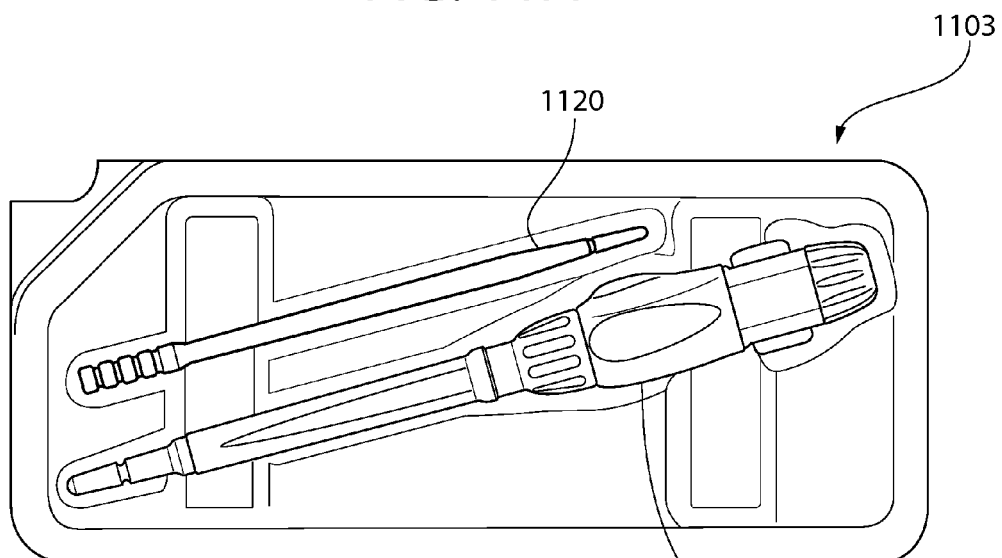
Figure 11C:
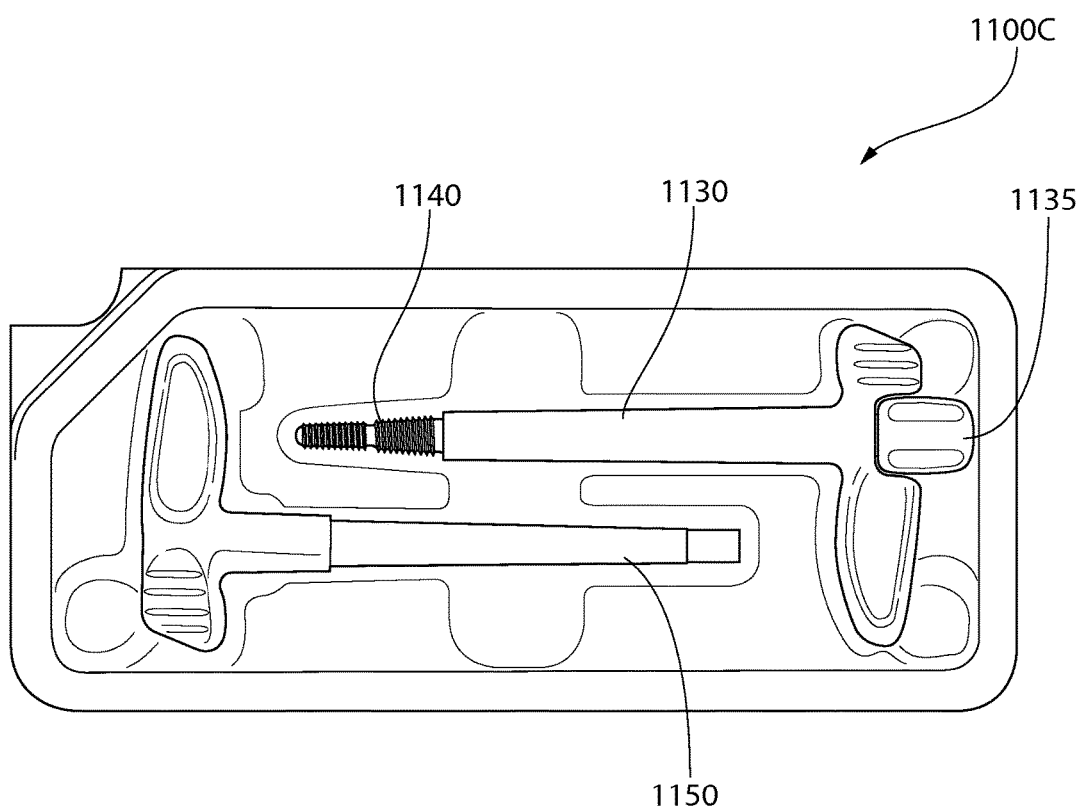

FIGS. 11A through 11C illustrate a multi-piece kit 1100, in accordance with an exemplary embodiment of the present invention. The multi-piece kit 1100 may be packaged in one or more polymer trays which allow for packaging and sterilization of the components in the multi-piece kit 1100.

FIG. 11A illustrates a first part 1100A of the kit 1100. The first part 1100A comprises a reamer 1110. FIG. 11B illustrates a second part 1100B of the kit 1100. The second part 1100B comprises the bone saw 100 and an implant place holder 1120. FIG. 11C illustrates a third part 1100C of the kit 1100. The third part 1100C comprises an implant driver 1130 preloaded with an implant 1140. The third part 1100C further comprises a jack screw driver 1150.

A method for using the components of the multi-piece kit 1100 is now described. A surgeon docks the trocar tip of the reamer 1110 against the bone at the pedicle 1010 entry site. The surgeon adjusts the trocar tip so that it is located at the anatomic center of the pedicle 1010. The surgeon brings the reamer 1110 in line with a fluoroscopic beam and taps the reamer 1100 with a mallet to seat the trocar tip into the bone over the center of the pedicle 1010. The surgeon then confirms correct localization of the trocar tip in the center of the pedicle 1010 using fluoroscopy. It is to be understood that the reamer 1110 matches the size of the implant 1140.

Using a back and forth rotational movement, the surgeon reams a passage through the pedicle 1010 until a cut mark 1105 of the reamer 1110 is located at the junction of the pedicle 1010 and the vertebral body 1020. The surgeon places the distal tip 101 of the bone saw assembly 100 into the reamed-out pedicle passage and aligns the notch 135 with the junction of the pedicle 1010 and the vertebral body 1020. The surgeon rotates the driver collar 800 one click (corresponding to 0.25 mm advancement of the saw blade 910) and makes a full circumferential cut. The surgeon then rotates the driver collar 800 and repeats the process until the saw blade tip 913 has been advanced 2 mm. Thereafter, the surgeon rotates the driver collar 800 360 degrees for each circumferential cut. The surgeon tracks progress using en face and lateral fluoroscopic views. The surgeon stops circumferential cutting when the narrowest diameter of the pedicle 1100 wall has been breached. The surgeon then shifts to zonal cutting.

Zonal cutting allows the thicker portions of the pedicle 1010 to be cut separately from the thinner areas. The surgeon moves the blade to the cranial portion of the pedicle 1010 and rotates the bone saw assembly 100 back and forth while advancing the blade in ¼ turn clockwise increments (1 click). The surgeon continues until the cranial portion of the pedicle 1010 is cut. The surgeon uses periodic fluoroscopic views (en face and lateral) to determine the position of the saw blade relative to the margins of the pedicle 1010. The surgeon retracts the blade 910 to move to a new zone such as the caudal portion of the pedicle 1010 and repeats the zonal cutting procedure. After cutting of the first pedicle 1010 is complete, the surgeon places the implant place holder 1120 to mark the place in the pedicle 1010 while the next pedicle 1010 is cut.

The surgeon places the implant 1140 into the pedicle 1010 passage and threads it inward with the implant driver 1130 until the mid-section of the implant 1140 (the portion having no threads) is aligned with the junction of the pedicle 1010 and the vertebral body 1020. The surgeon confirms correct positioning of the implant 1140 fluoroscopically.

The surgeon unthreads and removes an implant retainer 1135 on the implant driver 1130 while holding the implant driver 1130 in place. The surgeon inserts the jack screw driver 1150 through a central passage of the implant driver 1130 and engages a jack screw of the implant 1140. The implant is lengthened by turning the jack screw driver 1150 while holding the implant driver 1130 in place. The surgeon confirms pedicle 1010 lengthening with lateral fluoroscopy.

The implant is tightened while holding the implant driver 1130 securely while applying a clockwise force of 6 Nm to the jack screw driver 1150. The surgeon then removes the implant driver 1130 and the jack screw driver 1150 from the patient 1000.

These and other advantages of the present invention will be apparent to those skilled in the art from the foregoing specification. Accordingly, it is to be recognized by those skilled in the art that changes or modifications may be made to the above-described embodiments without departing from the broad inventive concepts of the invention. It is to be understood that this invention is not limited to the particular embodiments described herein, but is intended to include all changes and modifications that are within the scope and spirit of the invention.

What is claimed is:

1. A bone saw assembly, comprising:
   a flexible saw blade comprising a distal end, a proximal end, and a distal tip comprising a cutting edge, wherein the flexible saw blade is rectangular in shape over at least a portion of a length thereof;
   a saw handle base;
   a saw shaft tip assembly comprising:
      an opening through which the flexible saw blade is advanced;
      a saw shaft tip comprising a channel including a distal end and a proximal end; and
      a saw channel insert disposed within the channel of the saw shaft tip to form a lumen within the channel, the lumen longitudinally defined at least in part by the channel of the saw shaft tip and by the saw channel insert, the lumen housing the flexible saw blade therein and therethrough; and
   a saw blade advancement mechanism coupled to the flexible saw blade configured to move the flexible saw blade.

2. The bone saw assembly of claim 1, wherein the lumen extends from the proximal end to the distal end of the channel, wherein the opening is located at the distal end of the channel.

3. The bone saw assembly of claim 1, wherein the saw channel insert is completely disposed within the channel, from the proximal end to the distal end of the channel.

4. The bone saw assembly of claim 1, wherein:
   the channel comprises a floor comprising a curved portion at a distal portion of the channel; and
   the saw channel insert comprises a bottom with a curved portion at a distal portion thereof, the curved portion of the channel complementing the curved portion of the saw channel insert to provide a uniformly deep lumen, between the saw shaft tip and the saw channel insert, from the proximal end to the distal end of the channel, the lumen housing the flexible saw blade therein and entirely therethrough.

5. A bone saw assembly, comprising:
   a flexible saw blade comprising a distal end, a proximal end, and a distal tip comprising a cutting edge, wherein the flexible saw blade is rectangular in shape over at least a portion of a length thereof;
   a saw handle base;
   a saw shaft tip assembly comprising:
      an opening through which the flexible saw blade is advanced;
      a saw shaft tip comprising a channel comprising a distal end and a proximal end; and
      a saw channel insert disposed within the channel of the saw shaft tip to form a lumen between the saw shaft tip and the saw channel insert; wherein:
         the channel of the saw shaft tip comprises a floor comprising a curved portion at the distal end of the channel;
         the saw shaft tip includes a curved abutment disposed on the curved portion of the floor of the channel of the saw shaft tip;
         the saw channel insert comprises a distal end, a proximal end, a floor comprising a curved portion at the distal end of the saw channel insert, and a groove disposed in the curved portion of the floor of the saw channel insert; and
         the groove is sized and shaped to complement the curved abutment; and
   a saw blade advancement mechanism coupled to the flexible saw blade configured to move the flexible saw blade.

6. The bone saw assembly of claim 5, wherein the groove is sized and shaped to complement the curved abutment to impart a concave shape to the distal tip of the flexible saw blade as it is advanced through the opening.

7. The bone saw assembly of claim 5, wherein the channel of the saw shaft tip comprises a pair of slots and the saw channel insert further comprises a pair of ridges sized to fit within the pair of slots of the channel of the saw shaft tip, respectively.

8. The bone saw assembly of claim 5, further comprising a trunnion at a distal end of the saw shaft tip, the trunnion located distally of the opening, the trunnion facilitating placement of the distal tip of the shaft to precisely locate a desired blade opening location.

9. The bone saw assembly of claim 5, wherein the saw blade advancement mechanism is further configured to:
move the flexible saw blade distally to longitudinally translate the saw blade within the saw handle base to cause the cutting edge to exit the opening, and
move the flexible saw blade proximally to longitudinally translate the saw blade within the saw handle base to cause the cutting edge to retract within the opening.

10. The bone saw assembly of claim 5, wherein the saw blade advancement mechanism comprises:
a feedback ring; and
a driver collar coupled to the flexible saw blade and configured to:
move the flexible saw blade distally to longitudinally translate the saw blade within the saw handle base to cause the cutting edge to exit the opening as the driver collar is rotated in a first direction, and
move the flexible saw blade proximally to longitudinally translate the saw blade within the saw handle base to cause the cutting edge to retract within the opening as the driver collar is rotated in a second direction.

11. The bone saw assembly of claim 10, wherein:
the feedback ring comprises one or more teeth; and
the driver collar comprises one or more teeth complementing the one or more teeth of the feedback ring.

12. The bone saw assembly of claim 10, further comprising a spring communicating with the feedback ring, wherein:
the feedback ring comprises one or more teeth,
the driver collar comprises one or more teeth complementing the one or more teeth of the feedback ring, and
the spring is configured to urge the feedback ring against the driver collar to oppose rotational movement of the feedback ring relative to the driver collar.

13. An implant kit for stabilizing a spinal column comprising:
a bone saw assembly according to claim 5;
a drive tool instrument configured to insert and tighten a spinal implant; and
a polymer tray allowing for packaging and sterilization of the bone saw assembly and kit components.

14. A bone saw assembly, comprising:
a flexible saw blade comprising a distal end, a proximal end, and a distal tip comprising a cutting edge, wherein the flexible saw blade is rectangular in shape over at least a portion of a length thereof;
a saw handle base;
a saw shaft tip assembly comprising:
an opening through which the flexible saw blade is advanced;
a saw shaft tip comprising a channel comprising a distal end and a proximal end; and
a saw channel insert disposed within the channel of the saw shaft tip to form a lumen between the saw shaft tip and the saw channel insert;
wherein the channel of the saw shaft tip comprises a pair of slots and the saw channel insert comprises a pair of ridges sized to fit within the pair of slots of the channel of the saw shaft tip, respectively; and
a saw blade advancement mechanism coupled to the flexible saw blade configured to move the flexible saw blade.

15. A bone saw assembly, comprising:
a flexible saw blade comprising a distal end, a proximal end, and a distal tip comprising a cutting edge, wherein the flexible saw blade is rectangular in shape over at least a portion of a length thereof;
a saw handle base;
a saw shaft tip assembly comprising an opening through which the flexible saw blade is advanced; and
a saw blade advancement mechanism coupled to the flexible saw blade, the saw blade advancement mechanism comprising:
a feedback ring; and
a driver collar coupled to the flexible saw blade, the saw blade advancement mechanism configured to:
move the flexible saw blade distally to longitudinally translate the saw blade within the saw handle base to cause the cutting edge to exit the opening as the driver collar is rotated in a first direction, and
move the flexible saw blade proximally to longitudinally translate the saw blade within the saw handle base to cause the cutting edge to retract within the opening as the driver collar is rotated in a second direction.

16. The bone saw assembly of claim 15, wherein:
the feedback ring comprises one or more teeth; and
the driver collar comprises one or more teeth complementing the one or more teeth of the feedback ring.

17. The bone saw assembly of claim 15, further comprising a spring communicating with the feedback ring, wherein:
the feedback ring comprises one or more teeth,
the driver collar comprises one or more teeth complementing the one or more teeth of the feedback ring, and
the spring is configured to urge the feedback ring against the driver collar to oppose rotational movement of the driver collar relative to the feedback ring.

18. The bone saw assembly of claim 17, wherein the spring, configured to urge the feedback ring against the driver collar to oppose rotational movement of the driver collar relative to the feedback ring, creates a pre-determined resistance, wherein the saw blade advancement mechanism is configured so that:
rotation of the driver collar relative to the feedback ring with a force exceeding the pre-determined resistance, in the first direction, causes the one or more teeth of the driver collar to incrementally and respectfully pass over and again engage the one or more teeth of the feedback ring, thereby incrementally, longitudinally, and distally advancing the flexible saw blade within the saw handle base to cause the cutting edge of the saw blade to exit the opening; and
rotation of the driver collar relative to the feedback ring with a force exceeding the pre-determined resistance, in the second direction, causes the one or more teeth of the driver collar to incrementally and respectfully pass over and again engage the one or more teeth of the feedback ring, thereby incrementally, longitudinally, and proximally retracting the flexible saw blade within saw handle base to cause the cutting edge of the saw blade to retract back into the opening.

19. The bone saw assembly of claim 18, wherein the saw blade advancement mechanism is further configured so that each incremental passing over and again engagement of the one or more teeth of the driver collar with the one or more teeth of the feedback ring provides:
- tactile feedback to a user; and
- a discrete amount of advancement or retraction of the flexible saw blade.

20. The bone saw assembly of claim 18, wherein the saw blade advancement mechanism is further configured so that rotation of the driver collar with the saw blade extended, out of the opening, against a bony material, where the bony material creates a resistance exceeding the pre-determined resistance, causes the one or more teeth of the driver collar to incrementally and respectfully pass over and again engage the one or more teeth of the feedback ring, therein creating a rotational and incremental turning of the driver collar relative to the saw blade, thereby serving as an indication that a pre-determined torque has been exceeded.

21. An implant kit for stabilizing a spinal column comprising:
- a bone saw assembly according to claim 15;
- a drive tool instrument configured to insert and tighten a spinal implant; and
- a polymer tray allowing for packaging and sterilization of the bone saw assembly and kit components.

* * * * *